US011013450B2

(12) United States Patent
Folkerts et al.

(10) Patent No.: US 11,013,450 B2
(45) Date of Patent: *May 25, 2021

(54) DIAGNOSIS OF BRAIN AND SPINAL CORD INJURY BY BULBOCAVERNOSUS REFLEX MEASUREMENT

(71) Applicant: UroVal, Inc., Manhattan, KS (US)

(72) Inventors: Debra J. Folkerts, Manhattan, KS (US); Karen Louise Finstrom McPhee, Williamsburg, VA (US); Gregory Ray Johnson, Nisswa, MN (US); Timothy Martin Gack, Walker, MN (US)

(73) Assignee: Uroval, Inc., Manhattan, KS (US)

( * ) Notice: Subject to any disclaimer, the term of this patent is extended or adjusted under 35 U.S.C. 154(b) by 965 days.

This patent is subject to a terminal disclaimer.

(21) Appl. No.: 15/668,761

(22) Filed: Aug. 4, 2017

(65) Prior Publication Data

US 2017/0347909 A1 Dec. 7, 2017

Related U.S. Application Data

(63) Continuation of application No. 15/213,696, filed on Jul. 19, 2016, now Pat. No. 9,730,605, which is a (Continued)

(51) Int. Cl.
*A61B 5/391* (2021.01)
*A61B 5/11* (2006.01)
(Continued)

(52) U.S. Cl.
CPC ............ *A61B 5/391* (2021.01); *A61B 5/1107* (2013.01); *A61B 5/296* (2021.01); *A61B 5/407* (2013.01);
(Continued)

(58) Field of Classification Search
CPC .......................... A61B 5/04882; A61B 5/1107
See application file for complete search history.

(56) References Cited

U.S. PATENT DOCUMENTS

| 3,933,147 A | 1/1976 | Du Vall et al. |
| 4,099,519 A | 7/1978 | Warren |

(Continued)

FOREIGN PATENT DOCUMENTS

| DE | 19906140 | 7/2000 |
| FR | 2601254 | 7/1986 |

(Continued)

OTHER PUBLICATIONS

"Electrical Stimulation in Incontinence", Incontinence References, International Functional Electrical Stimulation Society, 2000, pp. 1-83.

(Continued)

*Primary Examiner* — Daniel L Cerioni
*Assistant Examiner* — Yasmeen S Warsi
(74) *Attorney, Agent, or Firm* — Sheridan Ross P.C.

(57) ABSTRACT

A system and method is disclosed for measuring muscle reflexes (e.g., a bulbocavernosus reflex) as a tool for identifying/diagnosing dysfunctions (e.g., spinal cord abnormalities, bladder voiding dysfunction, and sexual organ dysfunction) non-invasively by using mechanical stimulation. The system and method includes a probe having a predetermined patient contacting portion, wherein when the contacting portion is moved into contact with a particular area of the patient (e.g., the patient's genitals), the contact induces a muscle reflex. The probe detects the pressure resulting from the contacting portion being abruptly and forcibly brought into contact with the particular area. Such detection is used to electronically initiate capture of electrical responses from a plurality of electrodes placed on the
(Continued)

patient's skin in proximity to the particular area. Such electrical responses are processed to determine characteristics of the patient's reflexes of one or more muscles adjacent to the electrodes.

15 Claims, 16 Drawing Sheets

Related U.S. Application Data continuation-in-part of application No. 13/892,546, filed on May 13, 2013, now Pat. No. 9,392,955, which is a continuation of application No. 12/324,726, filed on Nov. 26, 2008, now Pat. No. 8,444,571, which is a continuation-in-part of application No. 12/238,433, filed on Sep. 25, 2008, now Pat. No. 8,439,845.

(60) Provisional application No. 60/975,056, filed on Sep. 25, 2007.

(51) Int. Cl.
| | |
|---|---|
| A61B 5/00 | (2006.01) |
| A61H 19/00 | (2006.01) |
| A61N 1/36 | (2006.01) |
| A61B 5/296 | (2021.01) |
| A61B 5/20 | (2006.01) |

(52) U.S. Cl.
CPC .......... *A61B 5/4064* (2013.01); *A61H 19/30* (2013.01); *A61N 1/36007* (2013.01); *A61B 5/202* (2013.01); *A61B 5/4368* (2013.01); *A61H 19/34* (2013.01); *A61H 19/40* (2013.01); *A61H 2201/10* (2013.01); *A61H 2201/1207* (2013.01); *A61H 2201/501* (2013.01); *A61H 2201/5043* (2013.01); *A61H 2201/5048* (2013.01); *A61H 2230/605* (2013.01)

(56) References Cited

U.S. PATENT DOCUMENTS

| | | | |
|---|---|---|---|
| 4,585,005 A | 4/1986 | Lue et al. | |
| 4,674,517 A | 6/1987 | Barnes et al. | |
| 4,759,377 A | 7/1988 | Dykstra | |
| 4,817,628 A | 4/1989 | Zealear et al. | |
| 4,881,526 A | 11/1989 | Johnson et al. | |
| 4,995,401 A | 2/1991 | Bunegin et al. | |
| 5,016,635 A | 5/1991 | Graupe | |
| 5,058,602 A | 10/1991 | Brody | |
| 5,086,779 A | 2/1992 | DeLuca et al. | |
| 5,142,183 A | 8/1992 | Burgess et al. | |
| 5,170,786 A | 12/1992 | Thomas et al. | |
| 5,259,388 A | 11/1993 | Eisman et al. | |
| 5,263,489 A | 11/1993 | Johnson et al. | |
| 5,318,039 A | 6/1994 | Kadefors et al. | |
| 5,329,194 A | 7/1994 | Dow et al. | |
| 5,435,282 A | 7/1995 | Haber et al. | |
| 5,505,208 A | 4/1996 | Toomim et al. | |
| 5,513,651 A | 5/1996 | Cusimano et al. | |
| 5,546,953 A | 8/1996 | Garfield | |
| 5,551,446 A | 9/1996 | Chutkow et al. | |
| 5,762,589 A | 6/1998 | Parker | |
| 5,775,331 A | 7/1998 | Raymond et al. | |
| 5,875,778 A | 3/1999 | Vroegop | |
| 5,875,788 A | 3/1999 | Loren | |
| 5,957,837 A | 9/1999 | Raab | |
| 6,047,202 A | 4/2000 | Finneran et al. | |
| 6,359,894 B1 | 3/2002 | Hong et al. | |
| 6,741,895 B1 | 5/2004 | Gafni et al. | |
| 6,862,480 B2 | 3/2005 | Cohen et al. | |
| 7,004,904 B2 | 2/2006 | Chalana et al. | |
| 7,041,059 B2 | 5/2006 | Chalana et al. | |
| 7,087,022 B2 | 8/2006 | Chalana et al. | |
| 7,367,956 B2 | 5/2008 | King | |
| 7,467,119 B2 | 12/2008 | Seidl et al. | |
| 7,914,468 B2 | 3/2011 | Shalon et al. | |
| 8,439,845 B2 | 5/2013 | Folkerts et al. | |
| 8,444,571 B2 | 5/2013 | Felkerta et al. | |
| 8,845,545 B2 | 9/2014 | Folkerts et al. | |
| 9,392,955 B2 | 7/2016 | Folkerts et al. | |
| 9,730,605 B2 | 8/2017 | Folkerts et al. | |
| 2004/0030360 A1 | 2/2004 | Eini et al. | |
| 2004/0147920 A1 | 7/2004 | Keidar | |
| 2005/0043608 A1 | 2/2005 | Haj-Yousef | |
| 2006/0004290 A1 | 1/2006 | Smith et al. | |
| 2006/0089824 A1 | 4/2006 | Siekmeier et al. | |
| 2006/0100668 A1 | 5/2006 | Ben-David et al. | |
| 2007/0099219 A1 | 5/2007 | Teverovskiy et al. | |
| 2007/0167812 A1 | 7/2007 | Lemmerhirt et al. | |
| 2015/0025409 A1 | 1/2015 | Folkerts et al. | |

FOREIGN PATENT DOCUMENTS

| | | |
|---|---|---|
| GB | 2284991 | 6/1995 |
| WO | WO 97/48446 | 12/1997 |
| WO | WO 02/065975 | 8/2002 |
| WO | WO 2007/089394 | 8/2007 |

OTHER PUBLICATIONS

"First Magnes Whole Head System is Up and Running at Scripps Clinic", MSI Advances; Fall 96 Issue, 4-D Neuroimaging, 3 pages.
"RMS Algorithm", http://en.wikipedia.org/wiki/Root_mean_square, Jan. 15, 2009, pp. 1-9.
Amarenco et al., "Dissociation between electrical and mechanical bulbocavernosus reflexes", Neurourology & Urodynamics, vol. 22(7), 2003, pp. 676-680.
Atkinson et al., "Subject Review Spinal Shock," Mayo clinic Proceedings, 1996, vol. 71, pp. 384-389.
Echlin et al., "A prospective study of physician-observed concussion during a varsity university ice hockey season: incidence and neuropsychological changes," Neurosurgical Focus, 2012, vol. 33(6), pp. 1-11.
Ertekin, et al. "The value of somatosensory-evoked potentials and bulbocavernosus reflex in patients with impotence", Acta Neurol Scand., 1985, 71(1), pp. 48-53.
Fowler, "A Neurologist's Clinical and Investigative Approach to Patients with Bladder, Bowel and Sexual Dysfunction", Neurology of Bladder, Bowel, and Sexual Dysfunction, vol. 1, 2001, pp. 1-6, chapter 1.
Gaetz et al., "Electrophysiological evidence for the cumulative effects of concussion," Brain Injury, 2000, vol. 14(12), p, 1077-1088, abstract only, 1 page.
Gosselin et al,, "Evaluating the cognitive consequences of mild traumatic brain injury and concussion by using electrophysiology," Neurosurgical Focus, 2012, vol. 33(6), pp. 1-7.
Henry (1994) The role of pudendal nerve innervation in female pelvic floor function. Curr. Opin. Obstet. Gynecol, 6, 324-325.
Kaiho et al., "Electromyographic study of the striated urethral sphincter by using the bulbocavernosus reflex: study of the normal voluntary voiding and the involuntary sphincter relaxation," Nippon Hinyokika Gakkai Zasshi, 1999. vol. 90(12), pp. 893-900, abstract only, 1 page.
Kaiho et al., "Bulbocavernosus reflex during the micturition cycle in normal male subjects," International Journal of Urology, 2004, vol. 11, pp. 33-37.
Kippers, "Electromyography (EMG)—Principles and Biological Bases", AN212 lecture, Mar. 14, 1999, pp. 1-13, The University of Queensland.
Lavoisier, et al. "Bulbocavernosus reflex: its validity as a diagnostic test of neurogenic impotence", Journal of Urology, Feb. 1989; 141(2): 311-4.
Livingston et al., "A preliminary investigation of motor evoked potentialabnormalities following sport-related concussion," Brain Injury, 2010, vol. 24(6), pp. 904-913, abstract only, 1 page.

(56) References Cited

OTHER PUBLICATIONS

Podnar, et al. "Mechanically evoked bulbocavernosus reflex and pudendal somatosensory responses in children," European Journal of Physiology, 1996, pp. R293-R294.
Prutchi, "A high-resolution large array (HRLA) surface EMG system", Med. Eng. Phys., 1995, vol. 17(6), pp. 442-454.
Sarica, et al. "Bulbocavernosus reflex to somatic and visceral nerve stimulation in normal subjects and in diabetics with erectile impotence", Journal of Urology, Jul. 1987; 138(1): 55-8.
Shafik, "Perineal nerve stimulation for urinary sphincter control", Urological Research, vol. 22, No. 3/ May 1994, Springer Berlin/Heidelberg, pp. 151-155.
Smith. "Scientist and Engineers Guide to Digital Signal Processing", 1997, Chapters 19 and 20, California Technical Publishing, San Diego, CA.
Tackmann, et al, "The bulbocavernosus reflex in controls and patients with potency disorders", Sep. 17, 1986, pp. 147-52, available at http://www.ncbi.nlm.nih.gov/pubmed/3095091.
Tepley, et al. "Magnetoencephalography (MEG)", Neuromagnetism Lab at Henry Ford Hospital, http://rambutan.phy.oakland.edu/~meg/, 2003, pp. 1-47.
Vereecken, et al. "Electrophysiological exploration of the sacral cones", vol. 227, No. 3/Jun. 1982, pp. 135-144.
Vodusek, et al. "EMG, single fibre EMG and sacral reflexes in assessment of sacral nervous system lesions", Journal of Neurological Neurosurgery Psychiatry, Nov. 1982; 45(11): 1064-6.
Waldron et al., "Evidence for motor neuropathy and reduced filling of the rectumin chronic intractable constipation," Gut, vol. 31, 1990, pp. 1284-1288.
Ziemann, et al. "Anal sphincter electromyography, bulbocavernosus reflex and pudendal somatosensory evoked potentials in diagnosis of neurogenic lumbosacral lesions with disorders of bladder and large intestine emptying and erectile dysfunction", Nervenarzt, 1996; 67(2): pp. 140-146, 8 pages.
International Search Report and Written Opinion for International (PCT) Application No. 08/77763, dated Nov. 28, 2008, 9 pages.
International Preliminary Report on Patentability for International (PCT) Patent Application No. PCT/US2008/077763, dated Apr. 8, 2010, 8 pages.
Extended EP Search Report for EP Application No. 08834484.1, dated Feb. 9, 2012, 11 pages.
Official Action for European Patent Application No. 08834484,1, dated Sep. 11, 2012 4 pages.
Official Action for European Patent Application No. 08834484.1, dated Oct. 16, 2013 4 pages.
Decision to Grant for European Patent Application No. 08834484.1, dated Mar. 19, 2015 1 page.
Official Action for U.S. Appl. No. 12/238,433, dated Oct. 18, 2011, 22 pages.
Official Action for U.S. Appl. No. 12/238,433, dated May 30, 2012 16 pages.
Notice of Allowance for U.S. Appl. No. 12/238,433, dated Nov. 27, 2012, 12 pages.
Notice of Allowance for U.S. Appl. No. 13/892,539, dated May 30, 2014, 7 pages.
Official Action for U.S. Appl. No. 12/324,726, dated Dec. 8, 2011, 17 pages.
Notice of Allowance for U.S. Appl. No. 12/324,726, dated Jan. 22, 2013, 9 pages.
Official Action for U.S. Appl. No. 15/213,696, dated Nov. 16, 2016, 5 pages.
Notice of Allowance for U.S. Appl. No. 15/213,696, dated Mar. 29, 2017, 8 pages.
Official Action for U.S. Appl. No. 14/484,590, dated Apr. 14, 2017, 6 pages.
Notice of Allowance for U.S. Appl. No. 14/484,590, dated Oct. 19, 2017, 8 pages.
U.S. Appl. No. 12/238,433, filed Sep. 25, 2008 now U.S. Pat. No. 8,439,845.
U.S. Appl. No. 13/892,539, filed May 13, 2013 now U.S. Pat. No. 8,845,545.
U.S. Appl. No. 14/484,590, filed Sep. 12, 2014.
U.S. Appl. No. 12/324,726, filed Nov. 26, 2008 now U.S. Pat. No. 8,444,571.
U.S. Appl. No. 13/892,546, filed May 13, 2013 now U.S. Pat. No. 9,392,955.
U.S. Appl. No. 15/213,696, filed Jul. 19, 2016 now U.S. Pat. No. 9,730,605.

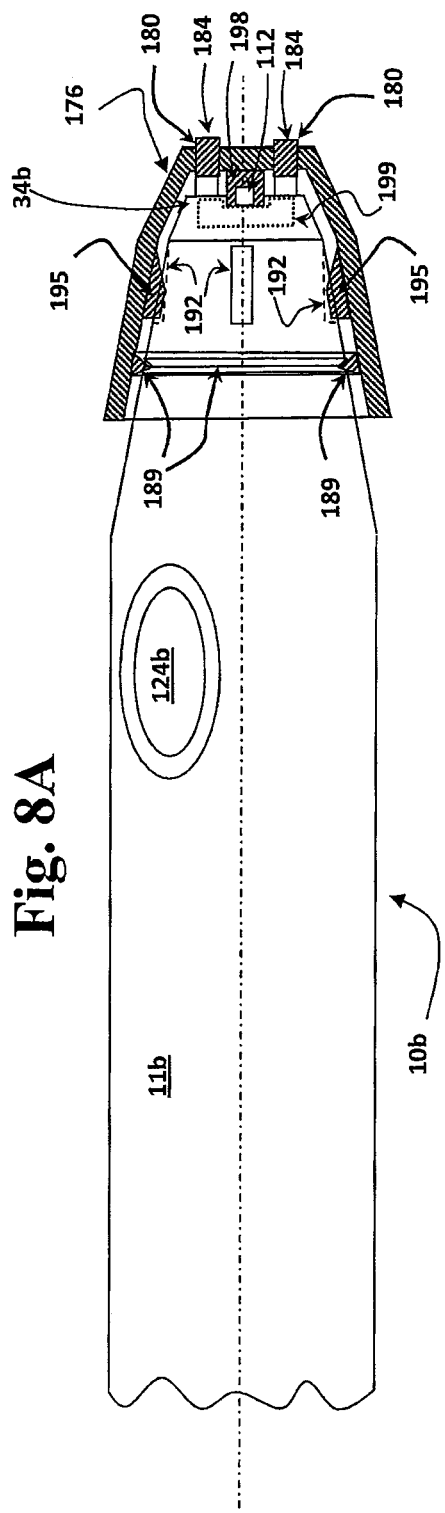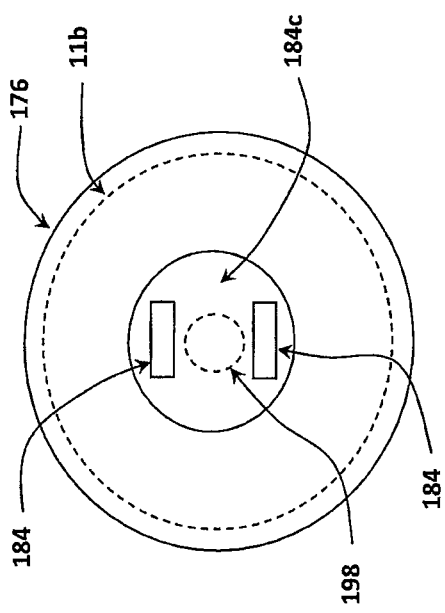

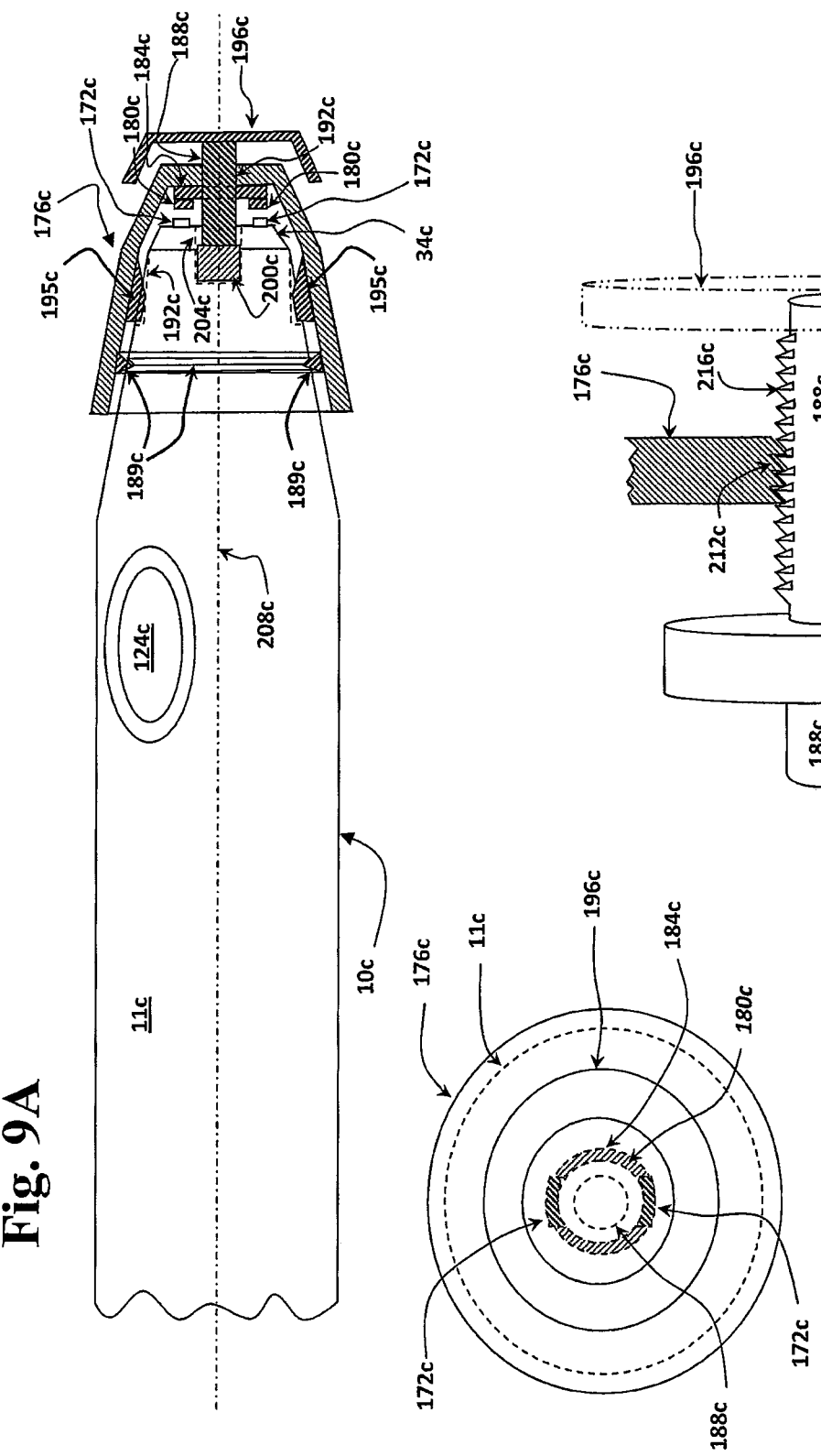
Fig. 9A
Fig. 9B
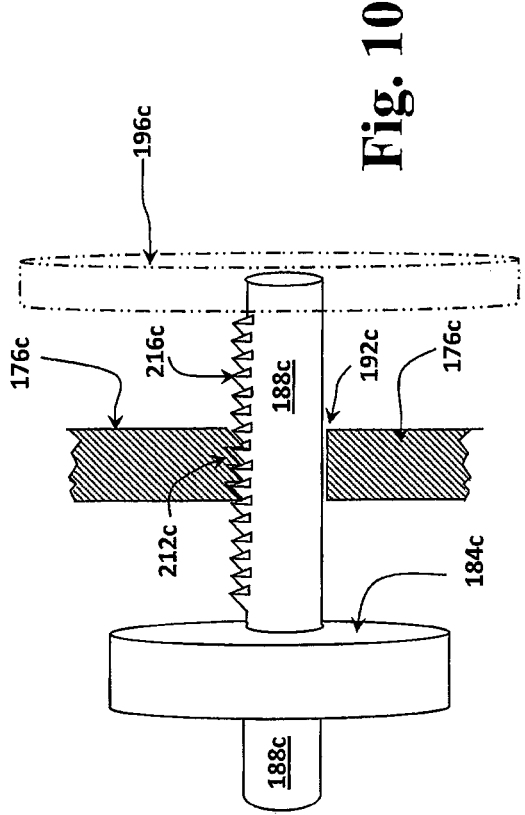
Fig. 10

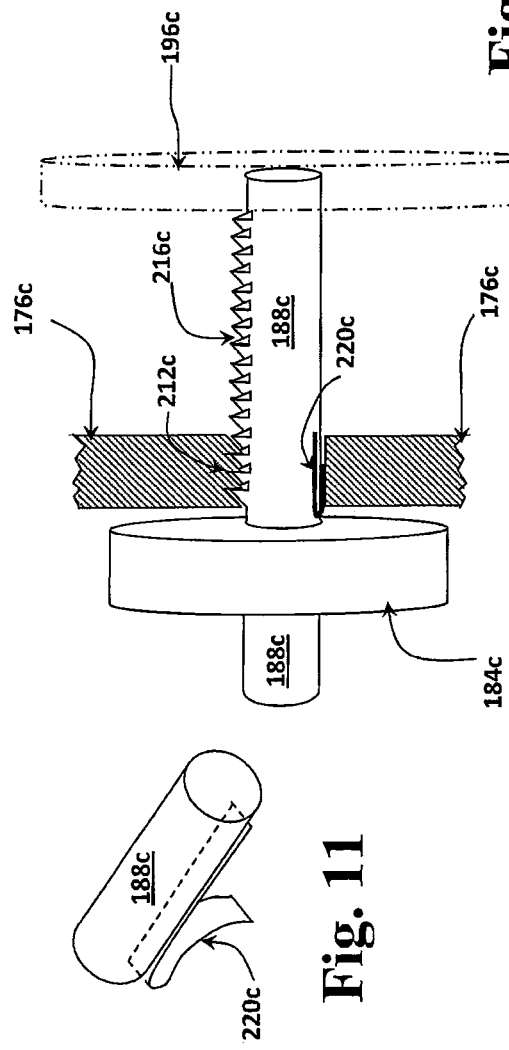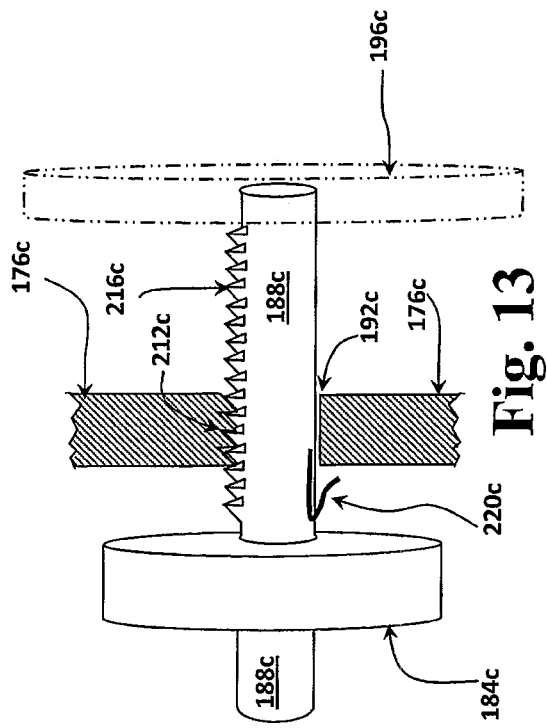
Fig. 11
Fig. 12
Fig. 13

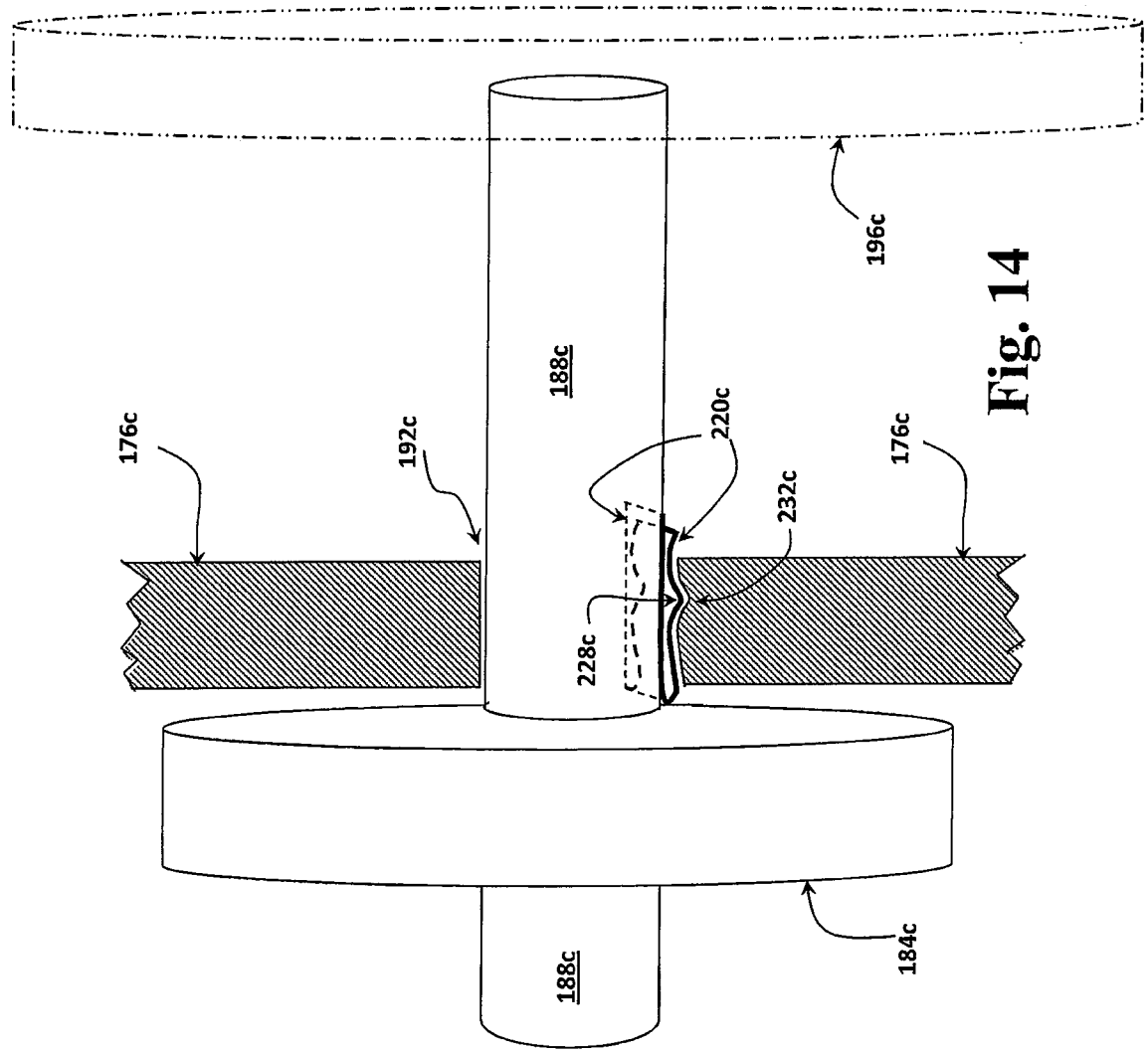

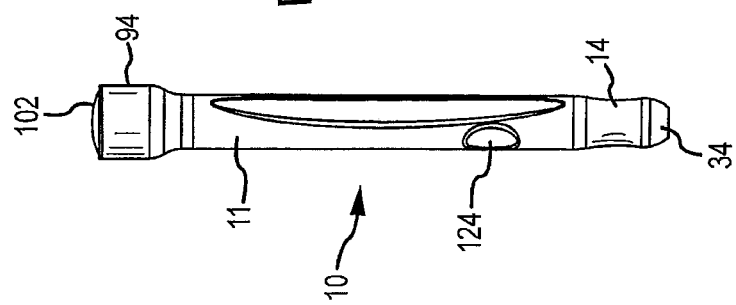
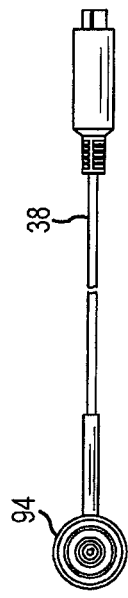
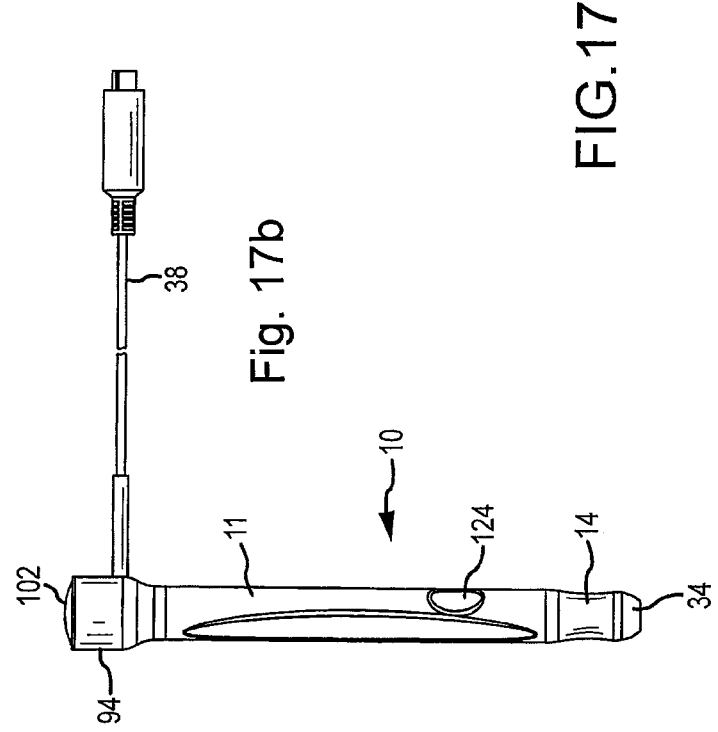
FIG. 17

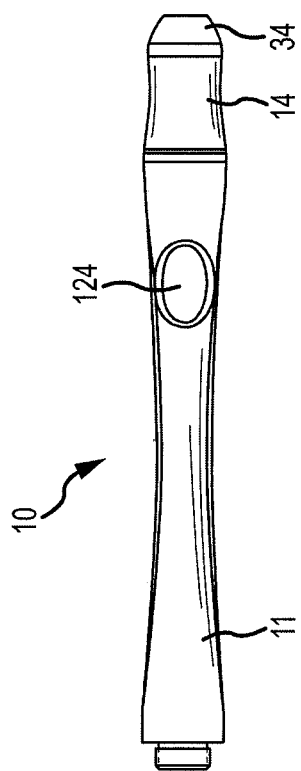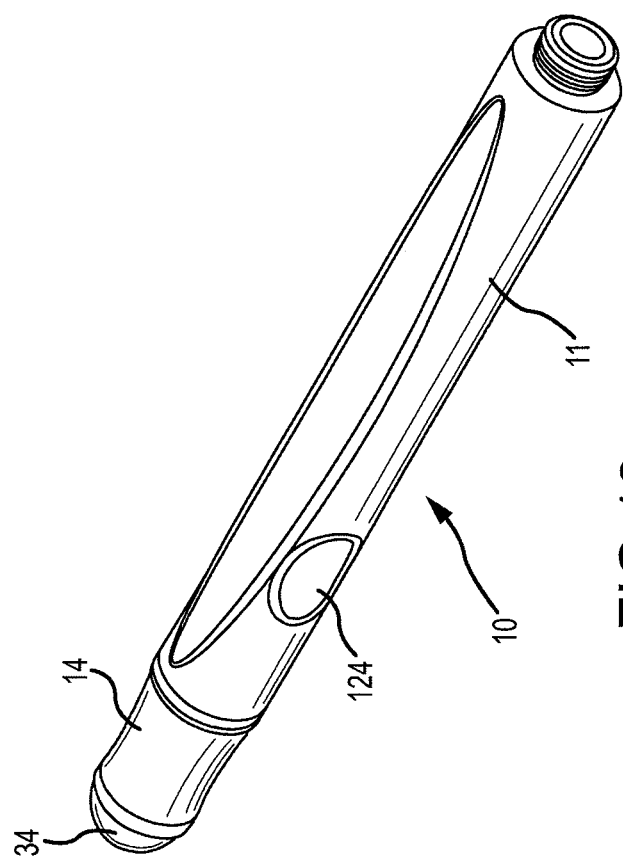
FIG.18
FIG.19

DIAGNOSIS OF BRAIN AND SPINAL CORD INJURY BY BULBOCAVERNOSUS REFLEX MEASUREMENT

CROSS-REFERENCE TO RELATED APPLICATIONS

This application is a continuation of U.S. patent application Ser. No. 15/213,696, filed Jul. 19, 2016 (now U.S. patent Ser. No. 15/213,696, issued Aug. 15, 2017), which is a continuation-in-part of U.S. patent application Ser. No. 13/892,546, filed May 13, 2013 (now U.S. Pat. No. 9,392,955, issued Jul. 19, 2016), which is a continuation of U.S. patent application Ser. No. 12/324,726, filed Nov. 26, 2008 (now U.S. Pat. No. 8,444,571, issued May 21, 2013), which is a continuation-in-part of U.S. patent application Ser. No. 12/238,433, filed Sep. 25, 2008 (now U.S. Pat. No. 8,439,845, issued May 14, 2013), which claims the benefit of U.S. Provisional Patent Application 60/975,056, filed Sep. 25, 2007. Each of the above-identified applications is incorporated herein by reference in its entirety.

FIELD OF THE INVENTION

The present disclosure relates to obtaining and processing data indicative of muscle reflexes for screening and/or diagnosing a patient with a brain injury or spinal cord injury, and especially for obtaining and processing data indicative of reflexes from the bulbospongiosus muscle. In particular, the present disclosure describes a novel electromechanical probe for stimulating the bulbospongiosus muscle, and consequently identifying a time of the stimulation so that electrical responses from electrodes on the patient's skin can be identified for analysis.

BACKGROUND OF THE PRESENT INVENTION

The bulbocavernosus reflex (BCR) is a contraction of the rectum that occurs when the tip of the penis or clitoris is squeezed or stimulated. The BCR is a polysynaptic reflex, and it is known that measurements of this reflex can provide indications of various neurological abnormalities in and around the pelvic floor and lower spinal region of a patient. For example, the integrity of the pudendal nerve and afferent and efferent nerve segments through the sacral vertebrae S2-S4 may be determined by measurements of the BCR. Additionally, several types of BCR abnormalities have been reported in cases of impotence secondary to lesions of the cauda equina or conus medullaris, or when neurogenic bladder dysfunction related to polyneuropathy is detected. Such abnormalities can manifest as no BCR response, a prolonged latency in BCR response, or a temporal latency dispersion occurring in repetitive measurements. Moreover, a BCR response, if prolonged, can be an indication of pelvic nerve damage in patients with pelvic floor disorders.

It is known that measurements of the BCR can be used to diagnose various pelvic floor disorders, including those disorders mentioned above. Such measurements may be collected from, e.g., urethral and/or anal sphincters after stimulation of the dorsal nerve of the penis or clitoris via activation of electrodes attached to a patient. Such measurements have additionally been obtained by electromyogram (EMG) testing.

Additionally, more recent research indicates that electrophysiological evaluation of sacral reflexes can identify neurologic causes of disturbance that do not originate in the pelvic floor or lower spinal cord, such as cerebral vascular accident, dementia, hydrocephalus, multiple sclerosis, lesions of the brain and/or upper spinal cord, and Parkinson's disease. Abnormalities in motor evoked potentials can also provide direct electrophysiological evidence for both short- and long-term effects of traumatic brain injuries, including concussions. Measurement of the BCR is particularly useful for diagnosis and management of trauma to the brain and spinal cord because, as a polysynaptic reflex, the BCR is one of the first reflexes to reappear after spinal shock.

Prior art procedures and apparatuses for obtaining BCR measurements have, however, been less than satisfactory in, e.g., their ease of use and the discomfort they cause patients. Accordingly, it is advantageous to have a non-invasive method and system for accurately detecting characteristics of BCR response, such as latency in response, lack of response, and abnormal reflex contractions, where such characteristics of the BCR are correlated with likely physiological and/or neurological dysfunctions.

BRIEF SUMMARY OF CERTAIN EMBODIMENTS OF THE INVENTION

It is one aspect of the present invention to provide a method for diagnosing at least one of a brain injury and a spinal cord injury, comprising providing a probe; abruptly contacting a patient's genital area with the shield cap of the probe, wherein a shaft of the cap slides along a longitudinal axis and thereby compresses an elastomeric component of the cap by an amount effective to cause an electrical conductor of the probe to contact a pair of electrodes that are spaced apart; detecting current flow between the electrodes to identify a time indicative of the cap contacting the patient for inducing a bulbocavernosus reflex; measuring a time delay of the bulbocavernosus reflex in the patient; and comparing the time delay of the bulbocavernosus reflex to a predetermined baseline, wherein, as a result of the abruptly contacting step, the electrical conductor moves toward a probe tip of the probe and slides past the pair of electrodes so that the flow of current between the electrodes ceases, and wherein the detecting step provides a signal effective for commencing the measuring step. In various embodiments, the probe comprises a housing with an opening therethrough, the housing operably associated with the probe tip; the patient contact shield cap, adapted to cover the probe tip and having the shaft with an expanded portion that prevents the shaft from sliding out of the opening in the housing; and the single electrical conductor attached to the expanded portion and concentric to the shaft, wherein the shaft of the cap is slidable along an axis within a bore through the cap, extends through the bore, is movable along the longitudinal axis, and has an inner end attached to the elastomeric component, the elastomeric component adapted to fit within the recess and exert a force effective to cause the expanded portion to contact the interior of the cap, wherein the inner end of the shaft and the elastomeric component are received in a recess within the probe and the shaft is slidable along the axis within the recess.

In certain embodiments, the method further comprises storing data indicative of a history of activation of the probe.

In certain embodiments, the cap further comprises a flat spring provided along the shaft, the flat spring adapted to fold against the shaft in a first position and move toward the probe tip in a second position.

In certain embodiments, the method further comprises determining information representative of at least one of a duration of the bulbocavernosus reflex, a value indicative of a magnitude of at least one electrical response of the bulbocavernosus reflex, and an attenuation in the electrical responses of the bulbocavernosus reflex.

In certain embodiments, the electrical conductor comprises an electrical switch.

In certain embodiments, the method further comprises determining a voltage difference between the electrodes.

In certain embodiments, the electrodes are placed on opposite sides of the patient's rectum.

In certain embodiments, the method further comprises identifying a length of time of the abruptly contacting step.

It is another aspect of the present invention to provide a method for diagnosing at least one of a brain injury and a spinal cord injury, comprising providing a probe comprising a housing with a bore therethrough, the housing comprising a piezoelectric disk, the disk electrically connected to an amplifier and activated by a power source; a stimulus plunger having first and second ends and a shaft that extends through the bore, the shaft being movable along a longitudinal axis and having an expanded portion that prevents the stimulus plunger from sliding out of an opening in the housing; and a compression spring that biases the second end of the stimulus plunger away from contact with the piezoelectric disk, wherein, when the stimulus plunger makes non-invasive contact with a patient's genital area, pressure from the stimulus plunger is transmitted to the genital area to induce a bulbocavernosus reflex; placing the stimulus plunger in non-invasive contact with the patient's genital area; activating the piezoelectric disk to generate an electromagnetic response indicative of the non-invasive contact; using the electromagnetic response to identify at least one electrical response indicative of the bulbocavernosus reflex from a plurality of electrodes placed on the patient's skin adjacent to the genital area; determining at least one quantity selected from the group of a time delay between the electromagnetic response and the at least one electrical response, a time duration of the at least one electrical response, a value indicative of a magnitude of the at least one electrical response, and an attenuation in the at least one electrical response; and comparing the quantity to a predetermined baseline.

In certain embodiments, the method further comprises storing data indicative of a history of activation of the probe.

In certain embodiments, the piezoelectric disk comprises an electrical switch.

In certain embodiments, the method further comprises determining a voltage difference between the plurality of electrodes.

In certain embodiments, the electrodes are placed on opposite sides of the patient's rectum.

In certain embodiments, the method further comprises identifying a length of time of the placing step.

While specific embodiments and applications of the present invention are illustrated and described, it is to be understood that the invention is not limited to the precise configuration and components disclosed herein. Various modifications, changes, and variations which will be apparent to those skilled in the art may be made in the arrangement, operation, and details of the methods and systems of the present invention disclosed herein without departing from the spirit and scope of the invention. It is important, therefore, that the claims be regarded as including any such equivalent construction insofar as they do not depart from the spirit and scope of the present invention.

The advantages of the present invention will be apparent from the disclosure contained herein.

For purposes of further disclosure and to comply with applicable written description and enablement requirements, the following references generally relate to methods, devices, and systems directed to electromyography, the use of electrodes to diagnose patient disorders, and the use of measurement of the bulbocavernosus reflex to assess patient dysfunctions, and are fully incorporated herein by reference:

U.S. Pat. No. 3,933,147, entitled "Apparatus and method for treating disorders in the region of the pubococcygeous muscle," issued 20 Jan. 1976 to Du Vall et al. ("Du Vall").

U.S. Pat. No. 4,099,519, entitled "Diagnostic device," issued 11 Jul. 1978 to Warren ("Warren").

D. B. Vodusek et al., "EMG, single fiber EMG and sacral reflexes in assessment of sacral nervous system lesions," 45(11) *Journal of Neurology, Neurosurgery and Psychiatry* 1064 (November 1982) ("Vodusek").

Cumhur Ertekin et al., "The value of somatosensory-evoked potentials and bulbocavernosus reflex in patients with impotence," 71(1) *Acta Neurologica Scandinavica* 48 (January 1985) ("Ertekin").

U.S. Pat. No. 4,585,005, entitled "Method and pacemaker for stimulating penile erection," issued 29 Apr. 1986 to Lue et al. ("Lue").

Y. Sarica and I. Karacan, "Bulbocavernosus reflex to somatic and visceral nerve stimulation in normal subjects and in diabetics with erectile impotence," 138(1) *Journal of Urology* 55 (January 1987) ("Sarica").

U.S. Pat. No. 4,674,517, entitled "Noninvasive ultrasonic probes," issued 23 Jun. 1987 to Barnes et al. ("Barnes").

P. Lavoisier et al., "Bulbocavernosus reflex: its validity as a diagnostic test of neurogenic impotence," 141(2) *Journal of Urology* 311 (February 1989) ("Lavoisier").

U.S. Pat. No. 4,817,628, entitled "System and method for evaluating neurological function controlling muscular movements," issued 4 Apr. 1989 to Zealear et al. ("Zealear").

U.S. Pat. No. 5,058,602, entitled "Paraspinal electromyography scanning," issued 22 Oct. 1991 to Brody ("Brody"). Brody describes a method of electromyographic scanning of paravertebral muscles comprising measuring electrical potentials bilaterally across segments of the spine. Readings are categorized into different patterns which are indicative of different muscular conditions. Brody suggests equipment useful within his described techniques as an available EMG scanner having electrodes spaced 2.5 cm apart and a computer component, but provides few details on the equipment or an indication of usefulness for isolating certain muscles or muscle groups.

U.S. Pat. No. 5,086,779, entitled "Back analysis system," issued 11 Feb. 1992 to DeLuca et al. ("DeLuca"). DeLuca describes a back analysis system of plural electrodes coupled to a computer system for processing the signals and to provide graphical representations of results. DeLuca's invention relates primarily to isolating particular muscle groups by the use of support and restraint devices which limit the movement of the patient's torso in predetermined patterns correlated to the desired muscle groups. DeLuca's electrode array consists of separate electrodes individually placed at desired locations on a patient's back.

U.S. Pat. No. 5,142,183, entitled "Electronic switch assembly," issued 25 Aug. 1992 to Burgess et al. ("Burgess").

U.S. Pat. No. 5,263,489, entitled "Relative electromyographic muscle reflex activity during motion," issued 23 Nov. 1993 to Johnson et al. ("Johnson").

U.S. Pat. No. 5,318,039, entitled "Method and an apparatus in electromyography," issued 7 Jun. 1994 to Kadefors et al. ("Kadefors"). Kadefors describes a method and apparatus for detecting electromyographic signals, processing them and providing an indication of the change of the signal from a predetermined norm. Kadefors' electrode system comprises three electrodes, one of which is a reference marker. This electronic apparatus, in essence, includes a sample and hold function in which current responses can be compared to earlier responses and an indication provided based on the differences detected.

U.S. Pat. No. 5,329,194, entitled "Ultrasonic peripheral vascular probe assembly," issued 12 Jul. 1994 to Dow et al. ("Dow").

U.S. Pat. No. 5,435,282, entitled "Nebulizer," issued 25 Jul. 1995 to Haber et al. ("Haber").

D. Prutchi, "A high-resolution large array (HRLA) surface EMG system," 17(6) *Medical Engineering and Physics* 442 (September 1995) ("Prutchi"). Prutchi describes a bracelet which may be wrapped about a body limb and which contains 256 surface electrodes to record the electrical activity of underlying muscles. The electrodes are arranged in eight groups of thirty-two electrode linear arrays directly connected to buffer boards in close proximity of the electrodes. Further processing of the electrical signals is performed to provide a desired signal analysis, in this instance primarily being concerned with the bidirectional propagation of a compound potential in a single muscle in the upper arm of a human subject or a histogram of total power contribution from active fibers in a subject muscle, both being presented in charted format.

U. Ziemann and C. D. Reimers, "Anal sphincter electromyography, bulbocavernosus reflex and pudendal somatosensory evoked potentials in diagnosis of neurogenic lumbosacral lesions with disorders of bladder and large intestine emptying and erectile dysfunction," 67(2) *Nervenarzt* 140 (February 1996) ("Ziemann").

Patty Pate Atkinson and John L. D. Atkinson, "Subject review: spinal shock," 71(4) *Mayo Clinic Proceedings* 384 (April 1996) ("Atkinson").

U.S. Pat. No. 5,505,208, entitled "Method for determining muscle dysfunction," issued 9 Apr. 1996 to Toomim et al. ("Toomim"). Toomim describes a method for determining the status of back muscles wherein EMG signals are monitored from a number of electrodes placed in a pattern on a patient's back, the activity of each electrode is determined and the results stored. A database of results provides a standard from which comparisons can be made to determine deviations or abnormalities, as a device for the care and management of the patient's dysfunction.

U.S. Pat. No. 5,513,651, entitled "Integrated movement analyzing system," issued 7 May 1996 to Cusimano et al. ("Cusimano"). Cusimano describes a portable electronic instrument for monitoring muscle activity, using standard ECG electrodes and a computer for analyzing the detected signals. The electrodes are applied individually at predetermined locations and a range of motion device is employed to generate signals related to a particular muscle group. Output plots are produced to provide an indication of results, apparently in the form of printouts of information reflecting any deviations from the norm of expected muscle activity.

U.S. Pat. No. 5,551,446, entitled "Reflex measuring device, and method," issued 3 Sep. 1996 to Chutkow et al. ("Chutkow").

U.S. Pat. No. 5,775,331, entitled "Apparatus and method for locating a nerve," issued 7 Jul. 1998 to Raymond et al. ("Raymond").

U.S. Pat. No. 5,957,837, entitled "Method and apparatus for wound management," issued 28 Sep. 1999 to Raab ("Raab").

U.S. Pat. No. 6,047,202, entitled "EMG electrode," issued 4 Apr. 2000 to Finneran et al. ("Finneran"). Finneran describes an electrode and array thereof for collecting surface electromyographic signals.

M. Gaetz et al., "Electrophysiological evidence for the cumulative effects of concussion," 14(12) *Brain Injury* 1077 (December 2000) ("Gaetz").

U.S. Pat. No. 6,359,894, entitled "Remote communications server system," issued 19 Mar. 2002 to Hong et al. ("Hong").

U.S. Patent Application Publication 2004/0030360, entitled "Intravaginal device for electrically stimulating and/or for sensing electrical activity of muscles and or nerves defining and surrounding the intravaginal cavity," published 12 Feb. 2004 to Eini et al. ("Eini").

U.S. Patent Application Publication 2004/0147920, entitled "Prediction and assessment of ablation of cardiac tissue," published 29 Jul. 2004 to Keidar et al. ("Keidar").

U.S. Patent Application Publication 2005/0043608, entitled "Method and apparatus for non-contact monitoring of cellular bioactivity," published 24 Feb. 2005 to Haj-Yousef ("Haj-Yousef").

U.S. Pat. No. 6,862,480, entitled "Pelvic disorder treatment device," issued 1 Mar. 2005 to Cohen et al. ("Cohen").

U.S. Patent Application Publication 2006/0004290, entitled "Ultrasound transducer with additional sensors," published 5 Jan. 2006 to Smith et al. ("Smith").

U.S. Patent Application Publication 2006/0089824, entitled "Methods and systems for drug screening and computational modeling," published 27 Apr. 2006 to Siekmeier et al. ("Siekmeier").

U.S. Patent Application Publication 2007/0099219, entitled "Systems and methods for treating, diagnosing and predicting the occurrence of a medical condition," published 3 May 2007 to Teverovskiy et al. ("Teverovskiy").

U.S. Patent Application Publication 2007/0167812, entitled "Capacitive micromachined ultrasonic transducer," published 19 Jul. 2007 to Lemmerhirt et al. ("Lemmerhirt").

Scott C. Livingston et al., "A preliminary investigation of motor evoked potential abnormalities following sport-related concussion," 24(6) *Brain Injury* 904 (June 2010) ("Livingston").

U.S. Pat. No. 7,914,468, entitled "Systems and methods for monitoring and modifying behavior," issued 29 Mar. 2011 to Shalon et al. ("Shalon").

Paul S. Echlin et al., "A prospective study of physician-observed concussion during a varsity university ice hockey season: incidence and neuropsychological changes," 33(6) *Neurosurgical Focus* E2 (December 2012) ("Echlin").

Nadia Gosselin et al., "Evaluating the cognitive consequences of mild traumatic brain injury and concussion by using electrophysiology," 33(6) *Neurosurgical Focus* E7 (December 2012) ("Gosselin").

As may be understood by those of ordinary skill in the art, certain components or features of the foregoing references may be incorporated and used in embodiments of the present disclosure. By way of non-limiting example, particular shapes or arrangements of probes, materials used to construct devices, or device sizes as disclosed in the prior art may be incorporated into embodiments of the present disclosure, and such uses are within the scope of this disclosure.

As used herein, "at least one," "one or more," and "and/or" are open-ended expressions that are both conjunctive and disjunctive in operation. For example, each of the expressions "at least one of A, B, and C," "at least one of A, B, or C," "one or more of A, B, and C," "one or more of A, B, or C," and "A, B, and/or C" means A alone, B alone, C alone, A and B together, A and C together, B and C together, or A, B, and C together.

It is to be noted that the term "a" or "an" entity refers to one or more of that entity. As such, the terms "a" (or "an"), "one or more," and "at least one" can be used interchangeably herein. It is also to be noted that the terms "comprising," "including," and "having" can be used interchangeably.

The embodiments and configurations described herein are neither complete nor exhaustive. As will be appreciated, other embodiments of the invention are possible utilizing, alone or in combination, one or more of the features set forth above or described in detail below.

BRIEF DESCRIPTION OF THE DRAWINGS

FIG. 1 shows the high level components of the novel apparatus for obtaining BCR measurements from electrodes (not shown) that are to be placed on a patient, wherein an exploded view of the probe 10 is shown.

FIGS. 8A and 8B show a different embodiment of the probe 10b for supplying BCR signals to the BRS module shown in FIG. 6. In particular, a non-reusable probe tip cap 176 is shown (in cross section in FIG. 8A) which can be attached to the probe 10b. The probed cap 176 contacts the patient and not the probe itself. Thus, the probe 10b can be reused with different patients. Note that FIG. 8B is an end view of the probe 10b and cap 176 combination as viewed from the patient contacting end of this combination.

FIGS. 9A and 9B show another embodiment of a probe (10c) and a corresponding probe tip cap (176c) for supplying BCR characteristic signals to a variation of the BRS module 108 shown in FIG. 6. Note that FIG. 9A shows a cross section of the cap 176c, and FIG. 9B shows an end view of the probe 10c and cap 176c combination as viewed from the patient contacting end of this combination.

FIG. 10 illustrates one technique for preventing reuse of the cap 176c, wherein mating slanted teeth (212c and 216c) engage for substantially assuring that once the patient contact shield 196c contacts a patient for inducing a BCR, the cap cannot be reused. Note that the dashed representation of the patient contact shield 196c as a disk is for simplicity of representation.

FIG. 11 shows a flat spring 220c attached to the shaft 188c, wherein the spring is also used to substantially assure that once the patient contact shield 196c contacts a patient for inducing a BCR, the cap cannot be reused.

FIG. 12 shows an embodiment of the cap 176c, wherein both the mating slanted teeth (212c and 216c) and flat spring 220c are used to substantially assure that once the patient contact shield 196c contacts a patient for inducing a BCR, the cap cannot be reused. In particular, this figure shows the flat spring 220c in a compressed configuration. Note that the dashed representation of the patient contact shield 196c as a disk is for simplicity of representation.

FIG. 13 illustrates the cap 176c of FIG. 12. However, in FIG. 13 the flat spring 220c is uncompressed, and accordingly prevents reuse of the cap 176c for obtaining signal characteristics of a BCR. Note that the dashed representation of the patient contact shield 196c as a disk is for simplicity of representation.

FIG. 14 shows another embodiment of the cap 176c, wherein the flat spring 220c is configured to also maintain the patient contact shield 196c in position for the contacting the patient when the spring is in a compressed configuration. Note that the dashed representation of the patient contact shield 196c as a disk is for simplicity of representation.

FIG. 15B shows an end view of the probe 10d and cap 176d combination as viewed from the patent contacting end of this combination.

FIG. 17a is a top perspective view of one embodiment of the present invention.

FIG. 17b is a perspective view of one embodiment of the present invention.

FIG. 17c is a side perspective view of one embodiment of the probe of the present invention.

FIG. 18 is a further perspective view of a related embodiment of the present invention.

FIG. 19 is a further perspective view of a related embodiment of the present invention.

DETAILED DESCRIPTION OF CERTAIN EMBODIMENTS OF THE INVENTION

Figure 1:
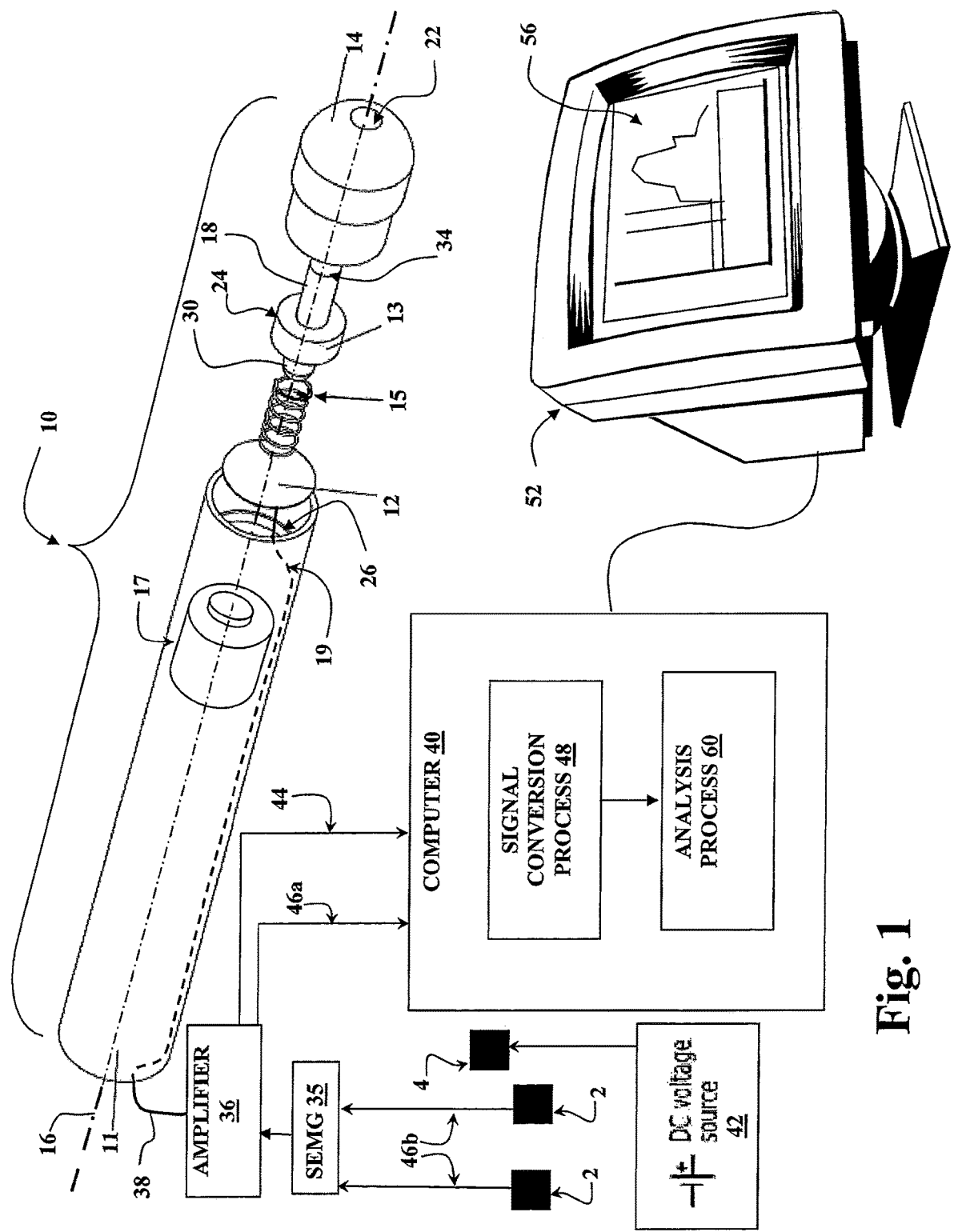
FIG. 1 shows an embodiment of the novel screening system and method disclosed herein. In particular.

It is one aspect of the present invention to provide a method for diagnosing at least one of a brain injury and a spinal cord injury, comprising providing a probe; abruptly contacting a patient's genital area with the shield cap of the probe, wherein a shaft of the cap slides along a longitudinal axis and thereby compresses an elastomeric component of the cap by an amount effective to cause an electrical conductor of the probe to contact a pair of electrodes that are spaced apart; detecting current flow between the electrodes to identify a time indicative of the cap contacting the patient for inducing a bulbocavernosus reflex; measuring a time delay of the bulbocavernosus reflex in the patient; and comparing the time delay of the bulbocavernosus reflex to a predetermined baseline, wherein, as a result of the abruptly contacting step, the electrical conductor moves toward a probe tip of the probe and slides past the pair of electrodes so that the flow of current between the electrodes ceases, and wherein the detecting step provides a signal effective for commencing the measuring step. In various embodiments, the probe comprises a housing with an opening therethrough, the housing operably associated with the probe tip; the patient contact shield cap, adapted to cover the probe tip and having the shaft with an expanded portion that prevents the shaft from sliding out of the opening in the housing; and the single electrical conductor attached to the expanded portion and concentric to the shaft, wherein the shaft of the cap is slidable along an axis within a bore through the cap, extends through the bore, is movable along the longitudinal axis, and has an inner end attached to the elastomeric component, the elastomeric component adapted to fit within the recess and exert a force effective to cause the expanded portion to contact the interior of the cap, wherein the inner end of the shaft and the elastomeric component are received in a recess within the probe and the shaft is slidable along the axis within the recess.

In certain embodiments, the method further comprises storing data indicative of a history of activation of the probe.

In certain embodiments, the cap further comprises a flat spring provided along the shaft, the flat spring adapted to fold against the shaft in a first position and move toward the probe tip in a second position.

In certain embodiments, the method further comprises determining information representative of at least one of a duration of the bulbocavernosus reflex, a value indicative of a magnitude of at least one electrical response of the bulbocavernosus reflex, and an attenuation in the electrical responses of the bulbocavernosus reflex.

In certain embodiments, the electrical conductor comprises an electrical switch.

In certain embodiments, the method further comprises determining a voltage difference between the electrodes.

In certain embodiments, the electrodes are placed on opposite sides of the patient's rectum.

In certain embodiments, the method further comprises identifying a length of time of the abruptly contacting step.

It is another aspect of the present invention to provide a method for diagnosing at least one of a brain injury and a spinal cord injury, comprising providing a probe comprising a housing with a bore therethrough, the housing comprising a piezoelectric disk, the disk electrically connected to an amplifier and activated by a power source; a stimulus plunger having first and second ends and a shaft that extends through the bore, the shaft being movable along a longitudinal axis and having an expanded portion that prevents the stimulus plunger from sliding out of an opening in the housing; and a compression spring that biases the second end of the stimulus plunger away from contact with the piezoelectric disk, wherein, when the stimulus plunger makes non-invasive contact with a patient's genital area, pressure from the stimulus plunger is transmitted to the genital area to induce a bulbocavernosus reflex; placing the stimulus plunger in non-invasive contact with the patient's genital area; activating the piezoelectric disk to generate an electromagnetic response indicative of the non-invasive contact; using the electromagnetic response to identify at least one electrical response indicative of the bulbocavernosus reflex from a plurality of electrodes placed on the patient's skin adjacent to the genital area; determining at least one quantity selected from the group of a time delay between the electromagnetic response and the at least one electrical response, a time duration of the at least one electrical response, a value indicative of a magnitude of the at least one electrical response, and an attenuation in the at least one electrical response; and comparing the quantity to a predetermined baseline.

In certain embodiments, the method further comprises storing data indicative of a history of activation of the probe.

In certain embodiments, the piezoelectric disk comprises an electrical switch.

In certain embodiments, the method further comprises determining a voltage difference between the plurality of electrodes.

In certain embodiments, the electrodes are placed on opposite sides of the patient's rectum.

In certain embodiments, the method further comprises identifying a length of time of the placing step.

In various embodiments, the screening system and method disclosed herein includes mechanical stimulation of the penis or clitoris performed by a novel probe 10, wherein a first embodiment of this probe is shown in FIG. 1. Preferred embodiments employ non-invasive probes, in contrast to numerous invasive systems and techniques of the prior art. In the embodiment of the probe 10 of FIG. 1 (shown in an exploded view), the probe includes a housing or handle 11, a piezoelectric disk or diaphragm 12, a stimulus plunger 13, a plunger housing 14, and a compression spring 15. When the probe 10 of FIG. 1 is assembled, the shaft 18 (of the stimulus plunger 13) extends through the bore or opening 22 of the plunger housing 14; however, since the expanded portion 24 of the stimulus plunger 13 cannot fit through the opening 22, this prevents this plunger from sliding out the opening 22. The piezoelectric disk 12 seats against a stop 26 within the generally cylindrical interior of the housing 11. The compression spring 15 biases an opposing end 30 of the stimulus plunger 13 away from contact with the piezoelectric disk 12. The piezoelectric disk 12 is electrically activated by a power source that may be internal or external to the probe 10. FIG. 1 shows an embodiment of the probe 10 wherein there is a battery 17 within the housing 11 for energizing the disk 12 in a conventional manner as one of ordinary skill in the art will understand. Additionally, there is an electrical conductor 19 in the probe 10 between the disk 12 and an external electrical conductor 38, wherein signals indicative of the opposing end 30 contacting the disk are conducted by the conductors 19 and 38 for amplification and establishing a commencement of data capture from the electrodes 2 as will be described in further detail hereinbelow. Note that the use of a piezoelectric disk may be important to embodiments of the probe 10 over other mechanisms for detecting when to commence data capture from the electrodes 2 since a piezoelectric disc has a very quick response time that is required due to the very brief response times encountered by the BCR (e.g., generally less than 200 milliseconds).

At a very high level, the probe 10 is used to contact the patient's clitoris or penis and in particular, a probe tip 34 (referred to more generally hereinabove as a "patient contacting portion") contacts the patient's clitoris or penis for thereby inducing a patient reflex response. The detection of the probe tip 34 contacting the clitoris or penis is accomplished by the probe 10 outputting an electrical signal indicative of the stimulus plunger 13 contacting the piezoelectric disk 12. The BCR in response to such contact is then detected by electrical signals output from properly positioned electrodes 2 on the patient's skin. Subsequently, such signals are amplified and then analyzed for determining/identifying characteristics of the amplified signals (and/or a graph thereof), wherein such characteristics may be used for identifying patient ailments and/or providing a patient diagnosis.

The compression spring 15, and plunger housing 14 restrain the stimulus plunger 13 in such a way that it can only move along the axis 16, and in particular, towards the piezoelectric disk 12 when the stimulus plunger tip 34 comes in contact with another object (e.g., a patient) with sufficient force to overcome the opposing force of the compression spring 15. Accordingly, when the stimulus plunger tip 34 comes in contact with a patient with such force so that the stimulus plunger 13 comes in contact with the piezoelectric disk 12 (while the disk is electrically activated), the disk distorts its shape (e.g., bends), and the mechanical stress caused by the stimulus plunger 13 contacting the piezoelectric disk 12 causes an electrical charge to develop on the surface of the piezoelectric disk 12. Since the disk 12 is electrically connected to an amplifier 36 (via the connection 19 and the external conductor 38), the electrical charge induced on the disk is detected by the amplifier for amplification (and at least in some embodiments, filtered as well via a high pass filter). Thus, the disk 12 functions as a sensor for detecting contact between a patient and the tip 34. However, alternative sensors may be used to detect the transfer of pressure from the tip 34 to the disk 12. In particular, the opposing end 30 may include a pressure sensitive switch (not shown) for detecting contact with the disk 12.

In one preferred embodiment, the probe 10 may be handheld by an operator for placing the probe in contact with a patient's penis or clitoris for initiating bulbocavernosus reflex. Moreover, in one preferred embodiment, the contact of the probe tip 34 with the patient's clitoris or penis is performed by an abrupt, non-invasive, pressure inducing motion that is preferably somewhat unexpected by the patient. Such a motion may be similar to inducing patellar reflexes during an examination of a patient's knee reflexes.

A battery 17 (e.g., internal to the probe), or a transformer (e.g., external to the probe, and not shown) may be used to electrically activate the disk 12 for detecting contact by the end 30 when genital simulation is performed via contact with the tip 34 of the shaft 18 (which extends through the bore 22).

Although such piezoelectric disks 12 may generate mechanical or pressure vibrations (i.e., oscillations in directions coincident with axis 16, FIG. 1), when electrically activated, wherein such vibrations may be transmitted to the tip 34, in at least some embodiments of the probe 10, any such vibrations are of substantially no consequence in inducing the genital stimulation. Said another way, the piezoelectric disk 12 is used only as a sensor for detecting the movement of the tip 34 when it contacts the patient for genital stimulation. However, additional/alternative methods of inducing such a BCR is also within the scope of embodiments disclosed herein. For example, the probe tip 34 may be vibratory such that the tip may first come in contact with the patient's clitoris or penis, and then commences a vibratory motion, wherein at the commencement of the vibratory motion, the probe 10 may output a signal indicative of the commencement of the vibratory motion. In particular, such contact prior to the onset of the vibratory motion may be relatively gentle and non-abrupt. It is believed that such vibratory motion may be provided by a piezoelectric disk 12 of appropriate manufacture.

The amplifier 36 (e.g., an EMG amplifier and high pass filter) amplifies the detected charge on the disk 12 induced by genital stimulation. The amplifier 36 responds by outputting a corresponding amplified response signal on the transmission cable 44 for transmission to a computer 40. The computer 40 is programmed to receive the probe 10 amplified signal as input, and assuming an electrical potential is being concurrently applied to the reference electrode 4 (e.g., via the DC voltage source 42), the amplified probe signal on the cable 44 act as a trigger to activate a signal conversion process 48 for commencing to sample the amplified electrode 2 signals output by the amplifier 36 via the surface electromyography (SEMG) unit 35. The computer 40 then converts the amplified signals from the electrodes 2 into a time series of numbers representing the magnitudes of the samples. In particular, the amplified electrode signals output on connection 46a are amplifications of the differences of signals derived from the sensing electrodes 2 (FIGS. 1 & 2) on wires 46b. In particular, the SEMG 35 receives the voltage signals from both of the electrodes 2 and forms a difference signal that is output to the amplifier 36.

Figure 2:
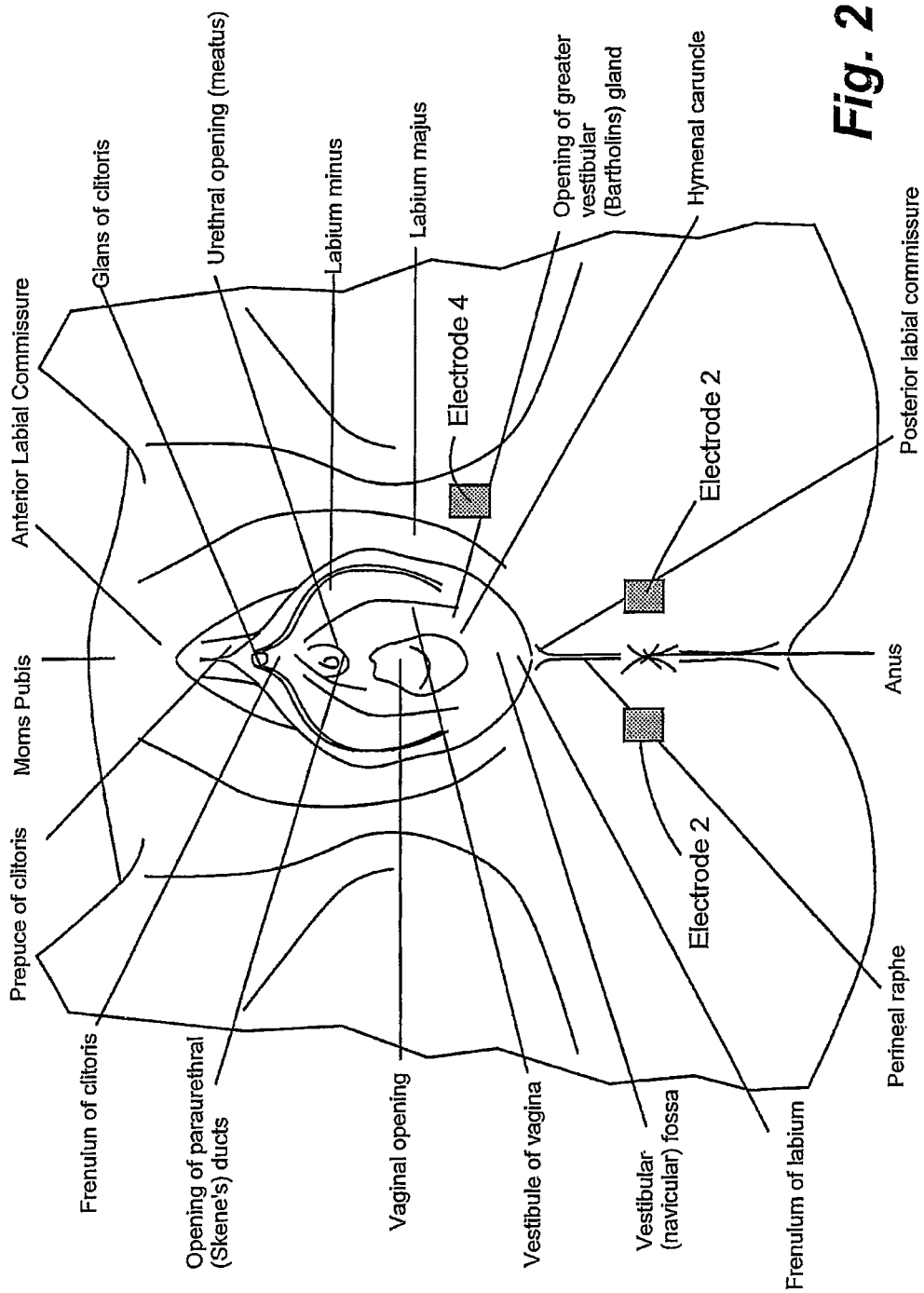
FIG. 2 shows one arrangement of the sensing electrodes 2 and the reference electrode 4 on a female patient for obtaining electrical signals for measuring BCR by the novel screening system and method disclosed herein.

As shown in FIG. 2, the sensing electrodes 2 may be placed at predetermined locations on a patient's body, e.g., at the 9 and 3 O'clock positions around a patient's rectum. Additionally, the reference electrode 4 may be positioned as also shown in FIG. 2 (e.g., in the patient's crotch area nearer to the genital area than the electrodes 2), or in some embodiments, the reference electrode 4 may be positioned on the patient's inner thigh (e.g., within six inches of the patient's genital area, and more preferably within 4 inches).

Note that the probe 10 (and in some embodiments, only the probe tip, as discussed in other sections hereinbelow) may be a single patient use device (i.e., non-reusable), e.g., the probe (or probe tip) is, in at least preferred embodiments, deactivated after it has been attached to the computer 40 for, e.g., an extended time period of such as 30 minutes. Such an extended time period gives an operator of the screening system and method ample time to obtain measurements of the bulbocavernosus reflex desired for the screening process. Note that when the probe 10 is battery powered such deactivation may be provided by a draining of the one or more batteries; e.g., once the probe is activated, current continues to flow from the one or more batteries until the batteries cannot power the probe. However, it is within the scope of the present disclosure that other methods of deactivating such batteries may be used, such as having an operator manipulate a deactivation switch that permanently disconnects the electrical power to the piezoelectric disk 12, or by providing an electronic timer in the probe 10 that activates with the first activation of the probe and deactivates the probe after a predetermined time has elapsed.

Amplified voltage signals derived from the difference of the signals output by the sensing electrodes 2 are provided to the computer 40, and in particularly, to the signal conversion process 48. The amplified voltage signals include signals representative of the potential (voltage) differences between the sensing electrodes 2 as determined by the SEMG 35.

However, in an alternative embodiment, the wires 46b may connect directly to the amplifier 36 for simply amplifying and outputting each of its input electrode 2 signals. In such an embodiment, the signal conversion process 48 computes values representative of the potential differences between the sensing electrodes 2. Note that the SEMG 35 is not required in this embodiment.

Using the output from the amplifier 36, the signal conversion process 48 performs an analog to digital conversion, wherein the signals on the connection 46a are sampled, digitized, and then the digitized samples are input to a computational procedure for generating a time series of records (e.g., a series of measurement records) representing the magnitude of the amplified signals over a predetermined elapsed time. More specifically, for each sampling period, the connection 46a is sampled, the obtained sample is used to determine a number in a predetermined range of, e.g., 0 to 4096, wherein the greater the number, the greater BCR, and wherein such numbers from different reference electrode voltages can be reliably compared, summed, averaged or otherwise combined if desired. Moreover, the values in this predetermined range may be then normalized to the range 0.0 to 1.0, as one of ordinary skill in the art will understand.

However, it is within the scope of the present disclosure that, instead of the resulting time series of BCR numbers being monotonic with the BCR, such numbers may be inversely related to the BCR. Accordingly, instead of 1.0 being indicative of a maximal BCR response as is computed in the steps above, 0.0 would be indicative of the maximal BCR response.

The time period between samplings may be, e.g., 1.0 millisecond, although alternative time periods that are smaller or larger are within the scope of the present disclosure.

In one embodiment of the screening system and method, an analog to digital converter separate from the computer 40 may receive the signals from the amplifier 36 for performing the signal conversion process 48.

However, regardless of where the analog to digital conversion is performed, subsequently the analysis process 60 described hereinbelow is performed.

The analysis process 60 may be instrumental in determining BCR patient data to be output to the display device 52 (FIG. 1), to a database (not shown), and/or to a report generator (not shown). In particular, the analysis process 60 may determine one or more of the following BCR related measures when provided with digital data output from the signal conversion process 48:

(a) a latency between the detection of the response signal on cable 44, and commencement of the BCR signals from the electrodes 2, (b) a duration of the BCR signals from the electrodes 2, (c) a value indicative of a magnitude or strength of the BCR, and/or (d) an attenuation in the magnitude or strength of the BCR (e.g., in comparison to an expected magnitude or strength).

Additionally, as described hereinbelow, the analysis process 60 may also determine associations between, e.g., values such as (a) through (d) immediately above, and likely a diagnosis of a patient's symptoms.

In order to more fully describe the processing and output of the analysis process 60, a description of a representative embodiment of output 56 (FIG. 1, and more particularly FIG. 5) from the analysis process is now described, wherein this output 56 is provided to a computer display device 52 operatively connected to the computer 40. In particular, referring to FIG. 5, a graph 62 may be displayed, wherein the horizontal (X) axis is elapsed time (in milliseconds), and the vertical axis represents signal magnitude values (preferably normalized to the range 0.0 to 1.0). A time value identified by the vertical line 64 on the graph 62 represents the detected application of the patient stimulus from the probe 10 as determined from the response signal on the cable 44. A subsequent time is identified by the vertical line 66 which represents the initial onset of the BCR in response to this stimulus. The Y (vertical) axis of the graph 62 represents the magnitude of a detected muscle (BCR) contractions. This magnitude is normalized in the range of 0.0 to 1.0 with 1.0 being the highest magnitude. The time series of normalized BCR response numbers is represented by the graphical signature 68. The horizontal line 72 is a reference line to facilitate viewing the graph 62. The auxiliary trace 74 is also for operator reference as well. In particular, the trace 74 provides the operator with a visual indication of all changes in voltage signals received from the electrodes 2 and the probe signals received on cable 44, wherein each change is shown by an upward movement in the trace 74. The values of the trace 74 may be computed as follows: $Y_n = X_n \cdot G$ where $G = 1/4096$, and $X_n$ is the nth BCR response value, and $Y_n$ is the normalized representation of the incoming time series, $X_n$ is the input signal, $G$ is the constant and $n$ is the time start to stop.

In one embodiment, the position of the line 66 is manually assigned by an operator, wherein, e.g., the operator is able to set (and/or select and drag) this line to the position the operator determines is most indicative the onset of the BCR. However, in an alternative embodiment, the position of the line 66 may be estimated by the screening system and method, e.g., by identifying an initial time where the graphical signature 68 remains above a predetermined threshold for a predetermined elapsed time.

A patient symptom can be entered in the interaction box 76, and the collected patient data, and/or measurements/characteristics derived therefrom, can be associated with this symptom. Accordingly, once an actual diagnosis of the cause of the symptom is determined for each of a plurality of patients, associations may be obtained between: (i) such actual diagnoses, and (ii) the symptoms and corresponding measurements/characteristics of the collected patient data (e.g., patient graphical signatures 68). In particular, such associations may become the basis for one or more predictive models for predicting a likely (if any) patient abnormality/diagnosis, wherein such associations may be formed by one or more of: a statistical method (e.g., a regression technique), a learning system (e.g., a vector machine, and an artificial neural network), and/or a pattern matching system (e.g., a fuzzy logic system, etc.). In particular, it is believed that such associations may be based substantially on the symptom identification together with one or more of the following BCR measurements:

(a) a latency between the graphical signature 68 (equivalently, the BCR signals from the electrodes 2), and the detection of the response signal on cable 44, (b) a duration of the graphical signature 68 (equivalently, the BCR signals from the electrodes 2), (c) a magnitude of the graphical signature 68 (equivalently, the BCR signals from the electrodes 2), (d) an attenuation in the magnitude of the graphical signature 68 (equivalently, the BCR signals from the electrodes 2), wherein such attenuation is, e.g., in comparison to an expected magnitude, and/or (e) no detectable graphical signature 68 (equivalently, the BCR signals from the electrodes 2).

Alternatively or additionally, the resulting time series of the digital data stream from the signal conversion process 48 can be input to an embodiment of analysis process 60 for hypothesizing a diagnosis for one or more conditions of the brain or spine. Such hypotheses may be generated by one or more hypothesis generating predictive models which are described hereinbelow.

Figure 5:
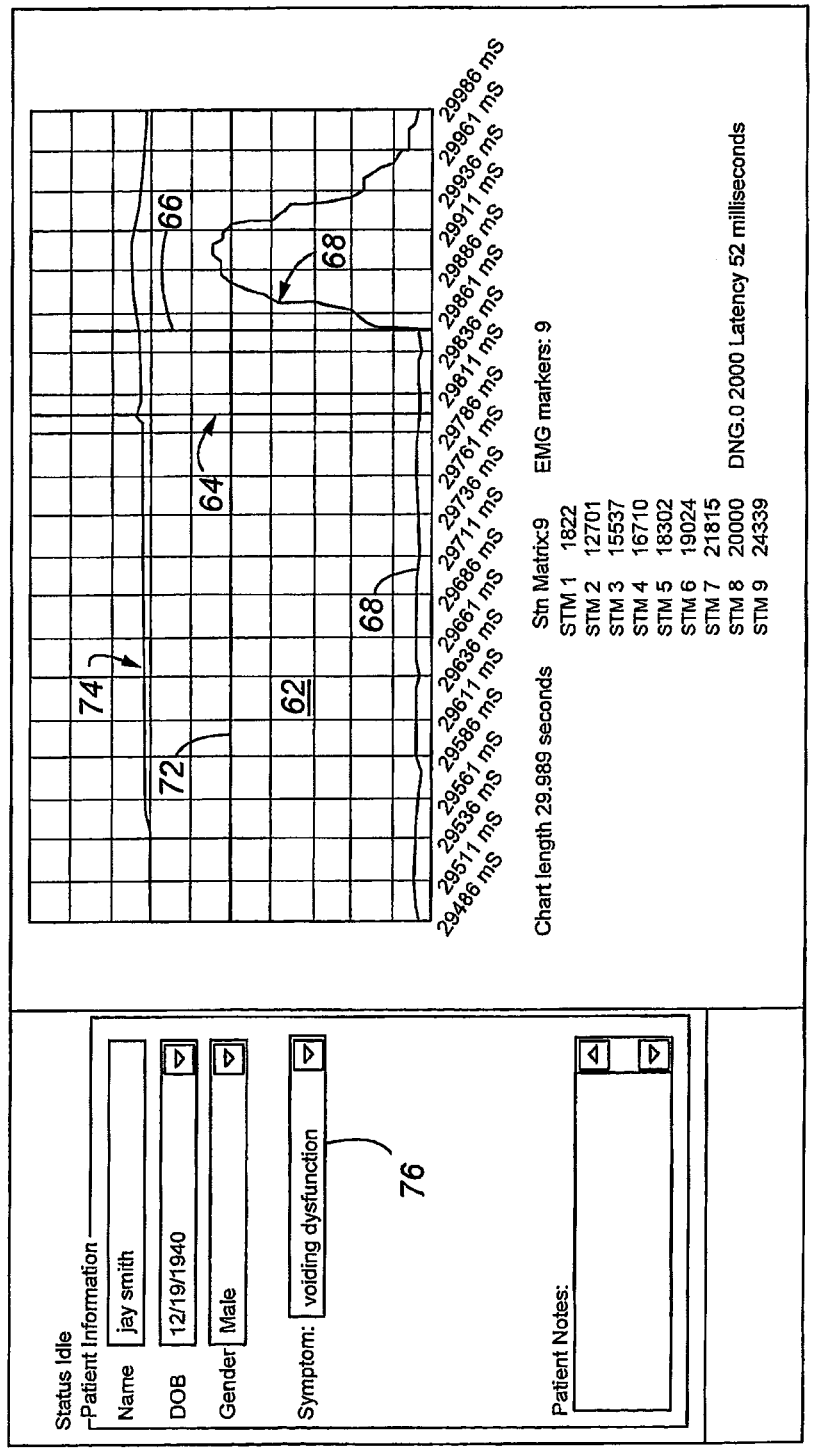
FIG. 5 shows an output screen for viewing BCR measurements, in particular, the following are shown: the magnitude and location of the applied stimulus (via the probe 10), the magnitude and time for a time series of responses to the stimulus, the time delay between the application of the stimulus and corresponding response(s).

In one such predictive model, a prolonged bulbocavernosus reflex of more than 45 msec., such as is shown in FIG. 5, may be considered indicative of a neurological disorder. More precisely, such a model may hypothesize one of the following disorders: sacral cord lesions, pudendal neuropathy (impotence, chronic back pain or disc disease), and lesions of the cauda equina. In one embodiment, prolonged such bulbocavernosus reflexes are determined by a calibration or training process, wherein time series BCR data is obtained from patients with such neurological disorders, and such data is used for determining parameters indicative of such disorders.

Additionally, such a model (or another model) may also identify an abnormal BCR latency, wherein such latency (e.g., in a range of 50+ msec.) may be indicative of the following disorders: diabetic neuropathy, or other, neurogenic disease process.

Moreover, such a model (or another model) may also provide output corresponding to an indication of a substantial absence or attenuation of the BCR within the predetermined sample time period for sampling the signals from the electrodes 2. In particular, such BCR absence or attenuation may be indicative of the following symptoms: sexual dysfunction, voiding dysfunction, and bowel dysfunction. Accordingly, the following may be considered likely diagnoses: decreased or absent sacral plexus response. Note that attenuation of the BCR in a graphical signature 68 also may be quantified as no bulbocavernosus response, particularly if such attenuation is below, e.g., a predetermined threshold such as a threshold corresponding to 2 micro volts above a baseline output from the muscle(s) at rest.

There are numerous measurements related to the graph 62 that may be determined to be effective for predicting patient disorders (i.e., diagnosing a patient's symptom(s)), and various calibration or training processes may be used to determine the measurements that are most effective in providing an appropriate diagnosis. In addition to the measurements/characteristics of the BCR patient data received from the signal conversion process 48, some additional measurements that may be useful in diagnosing a patient's symptoms are: the integral of the graphical signature 68, the number or magnitude of local minima or maxima, an extent of the graphical signature 68 below/above a predetermined value, etc.

In one embodiment of the presently disclosed system and method for screening, instead of (or in addition to) hypothesizing/diagnosing various disorders/symptoms, any of the above mentioned statistics or characteristics of the graphical signature 68 may be computed from the BCR digital data streams, and then output to a technician, nurse or physician for review and interpretation.

In one embodiment of the screening system and method, one or more of the following assessments may be obtained from analysis of the BCR time series measurements generated by the signal conversion process 48:

(a) the patient's spinal cord segments S2 through S4 are intact, (b) there may be lesions in the cauda equina, (c) an indication of actual chronic back pain, e.g., as asserted by the patient, (d) the latency between genital stimulation and the resulting bulbocavernosus reflexes are within a normal range and are not indicative of neurological order (e.g., contrary to what is asserted by the patient), (e) the latency between genital stimulation and the resulting bulbocavernosus reflexes are abnormal and are indicative of a neurological disorder, (f) the BCR time series measurement are indicative of a voiding dysfunction, bowel dysfunction, and/or (g) the time series measurements are indicative of a male impotence condition.

A report may be generated by the analysis process 60, and the report can be included, e.g. printed, for entry into the patient's medical records, wherein the report may include any of the information disclosed hereinabove.

Figure 3:
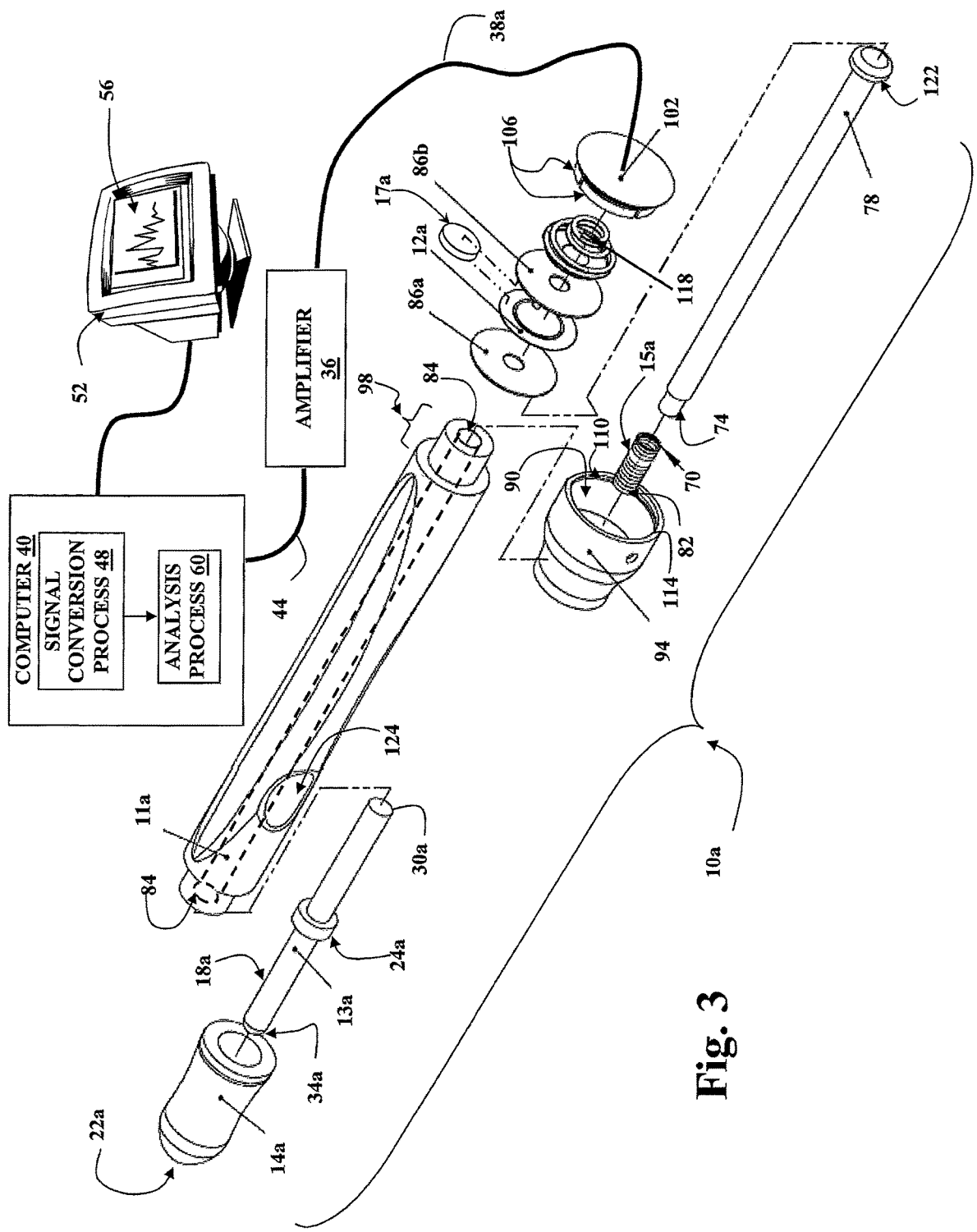
FIG. 3 shows the components of another embodiment of the novel screening system and method, wherein an exploded view of the probe 10a is shown.
Figure 4:
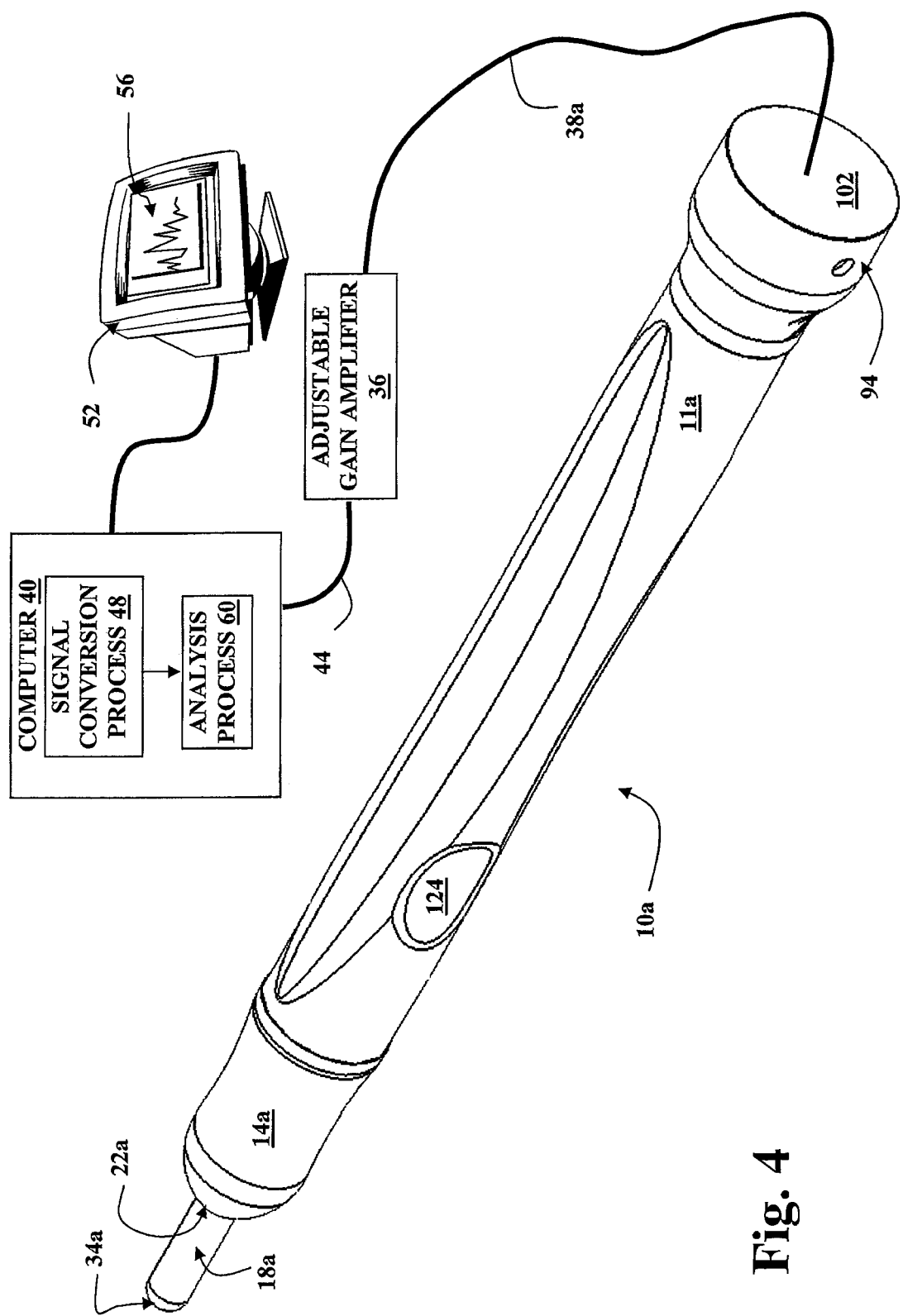
FIG. 4 shows the embodiment of FIG. 3 with the probe 10a fully assembled.

Another embodiment of the probe is shown in FIGS. 3 and 4, wherein components that functionally correspond to components of probe 10 described hereinabove are identified by the same numerical label except with an "a" following. Accordingly, the probe is identified by the label "10a".

One or more of FIGS. 3 and 4 show:

(i) a handle 11a for holding the probe 10a, (ii) a piezoelectric disk 12a for at least detecting a mechanical pressure from the tip 34a for stimulating a patient's penis or clitoris in a similar manner as discussed hereinabove.

(iii) a stimulus plunger 13a for transferring toward the piezoelectric disk 12a a resulting mechanical movement of the tip 34a contacting the patient's penis or clitoris; in particular, the plunger 13a includes the tip 34a, and an opposing end 30a, (iv) a plunger housing 14a which is operatively attached to an end of the handle 11a for retaining at least part of the stimulus plunger 13a therein; note that as with the plunger housing 14 of the probe 10, the plunger housing 14a includes an opening or bore 22a through which the shaft 18a of the stimulus plunger 13a extends, and the stimulus plunger 13a (as with the stimulus plunger 13) includes an expanded portion 24a that prevents the plunger from slipping entirely through the opening 22a, (v) a compression spring 15a for separating the stimulus plunger 13a from the piezoelectric disk 12a; in particular, the end 70 of the spring 15a fits onto an end 74 of the pressure transfer rod 78, and the spring end 82 contacts the opposing end 30a of the plunger 13a within the channel 84 extending the length of the handle 11a.

When the probe 10a is fully assembled, the piezoelectric disk 12a is sandwiched between washers 86a,b (preferably plastic). The disk 12a and washers 86 are contained within an interior 90 of the piezohousing 94 which is secured to the end 98 of the handle 11a by, e.g., adhesive, mating threads, a snap fit, or another comparable securing mechanism. An endcap 102 seals the disk 12a and the washers 86a and 86b within the interior 90 by, e.g., snapping the semi-annular locking projections 106 onto the ridge or recess 110 adjacent the opening 114 of the interior 90. Additionally retained in the interior 90 is a tapered compression spring 118 which provides a pressure on the piezoelectric disk 12a at all times. When the pressure transfer rod 78 is positioned in the channel 84, the expanded head 122 rests against the center opening in the washer 86a, but the expanded head is too large to fit through this opening.

During operation of the probe 10a, an operator activates the probe 10a by, e.g., a quick downward (preferably at least somewhat unanticipated) pressure of the stimulus tip 34a on the clitoris or penis. In one embodiment, when electrical power is already being supplied to the disk 12a from an electrical power source, e.g., a battery 17a (preferably positioned between the disk 12a and the washer 86b) within the handle 11a, or an exterior electrical power supply (not shown), such activation of the probe by contacting a patient's genital area causes the end 74 of the transfer rod 78 and the opposing end 30a to come in contact (or otherwise become configured for the transfer of tip 34a movement). Accordingly, the movement of the tip 34a toward the interior of the plunger housing 14a causes movement of the transfer rod 78 for increasing pressure on the disk 12a, wherein such increased pressure results in an additional electrical charge to develop on the surface of the piezoelectric disk. Since the disk 12a is electrically connected to the amplifier 36 (via a connection not shown, and the external conductor 38a), the electrical charge induced on the disk is detected by the amplifier for amplification. Thus, the disk 12a functions as a sensor for detecting contact between a patient and the tip 34a. However, note that alternative embodiments of sensors may be used to detect the transfer of pressure from the tip 34a to the disk 12a. In particular, the opposing end 30a may include a pressure sensitive switch (not shown) for detecting contact with the disk 12a.

Alternatively, such activation of the probe 10a by contacting a patient's genital area may initiate an electrical current from a power source (e.g., a battery 17a, or an exterior electrical power supply) to the piezoelectric disk 12a thereby causing the disk to apply vibratory pressure to the transfer rod 78 for initiation of the BCR reflex. Thus, when the tip 34a is pressed against the penis or clitoris, the shaft 18a slides further into the plunger housing 14a and handle 11a for thereby compressing the spring 15a so that vibratory pressure from the disk 12a results in mechanical vibrations being transferred to the tip 34a (via the shaft 18a and the transfer rod 78) for stimulation of the penis or clitoris.

As with the probe 10, at the time that the vibratory pressure commences to transfer to the tip 34a, a mechanical stress caused by the head 122 applying additional pressure against the disk 12a causes an electrical charge to develop on the surface of the disk. This electrical charge is communicated to the external conductor 38a via an internal conductor (not shown), and subsequently conveyed to the amplifier 36 (e.g., an EMG amplifier) where it is detected, and amplified as described hereinabove. The amplified signal is transmitted to the computer 40 (via transmission cable 44) as also described hereinabove.

Accordingly, the probe (10 or 10a) at least provides electrical signals for identifying when to commence measuring an electrical response (via the sensing electrodes 2) to a BCR.

In each of the above embodiments of the probe 10 and 10a, the included disk (or other vibration generating element) may be selected for generating vibrations having frequencies in the range of 2 Hz to 20 Hz, and more preferably in the range of 4 Hz to 10 Hz, most preferably approximately 5 Hz. In particular, the inventors have determined that vibrations outside of these ranges have reduced effect on the patient, and/or may be painful.

Note that in addition to activation of the probe (10 or 10a) by contacting a patient's genital area, the probe may include an activation switch (e.g., button switch 124, FIG. 3), wherein pressing (or otherwise manipulating) such a switch induces a current to flow to the disk 12a for providing an electrical potential to the disk. Such a switch may only activate the electrical features of the probe, and not be capable of turning off such features. Accordingly, as described hereinabove, a battery powered embodiment of the probe may be used for only a prescribed time before becoming non-functional due to, e.g., one or more dead batteries. However, other mechanisms may also be used for prohibiting the reuse of the probe with another patient. For example, a deactivation timer may be incorporated into the probe.

Note that for embodiments of the probe wherein the included disk remains in a vibratory active state once the probe is powered on, such vibrations (or lack thereof) can be an indicator to an operator as to whether the probe has been previously used. For example, if upon activation of the activation switch, the operator senses no vibratory response from the disk 12 or 12a (e.g., due to a dead battery, and/or due to detection that the activation switch has been previously used to power the probe, etc.), then the operator will be alerted that the probe is at least non-functional and may have been used previously.

Moreover, at least some embodiments, the probe (10 or 10a) may include a light emitting diode to notify an operator that the probe has not been previously used. For example, for a functional probe that had not been previously activated, such a diode would be activated when the button switch 124 is pressed for electrically activating the probe, and such a diode would emit light until a predetermined probe state occurs that deactivates the probe and prevents the probe from being reactivated.

Embodiments of the probe (10 or 10a) may also prohibit their reuse based not only on an elapsed time, but also on the number of times the probe tip is depressed toward the interior of the probe housing. For example, by providing no more than, e.g., five probe tip depression within a predetermined maximal elapsed time of probe activation, additional assurance that the probe will not be reused with another patient can be provided.

Figure 6:
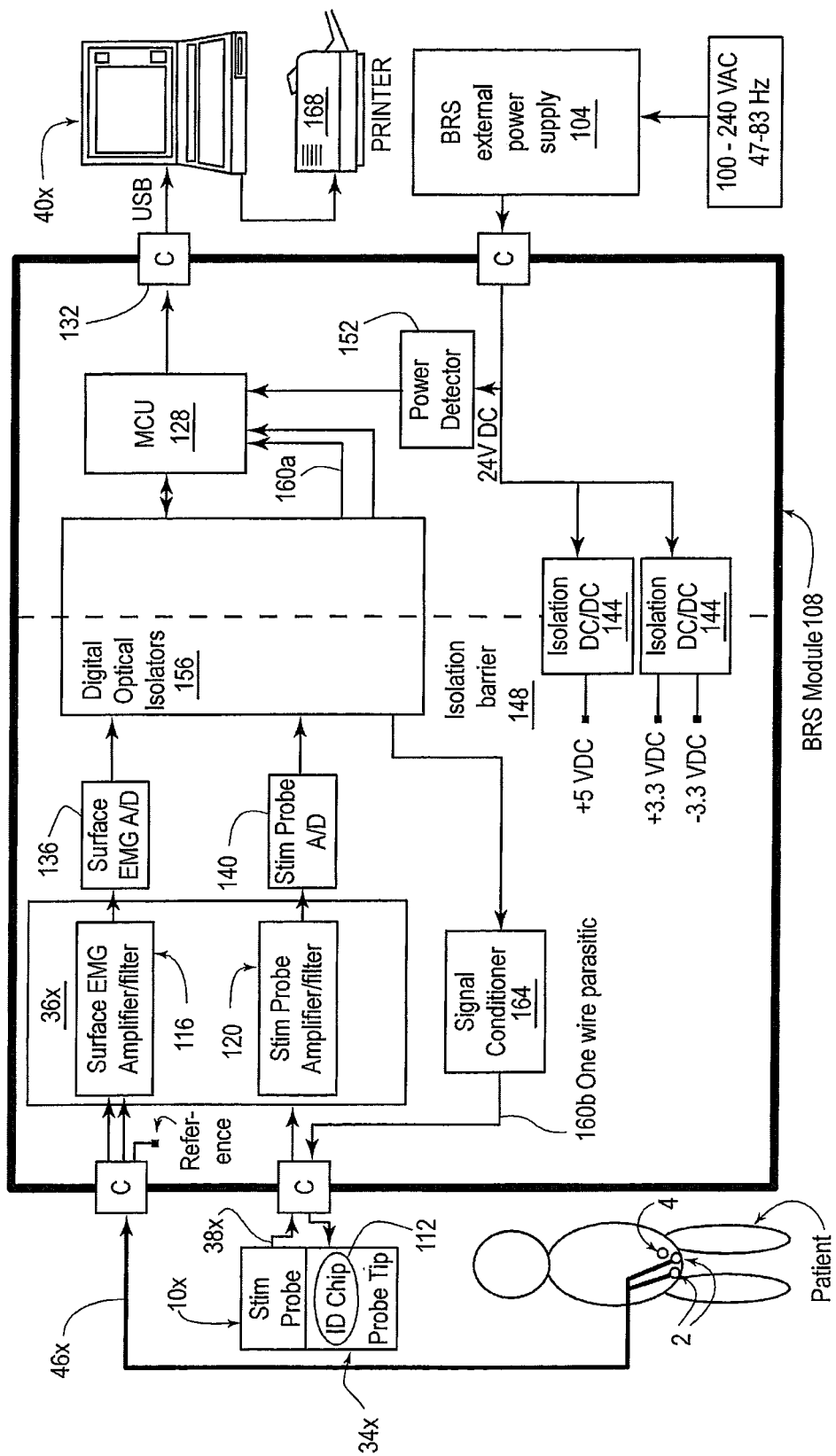
FIG. 6 shows a block diagram of another embodiment of the screening system and method disclosed herein.

Referring now to FIG. 6, a more detailed diagram of an embodiment of the screening system and method is disclosed. The components (and communications therefor) described in FIG. 6 that have substantially identical functionality with components described hereinabove are identified by the number of the component described above followed by "x". Moreover, an embodiment of the probe 10x shown in FIG. 6 may be one of: probe 10 or 10a, or another embodiment. The components, communications, and data processing of the embodiment of FIG. 6 are described in the following sections (1) through (7).

(1) Description of the Components Shown in the Embodiment of FIG. 6.

(1-1) A Bulbocavernosus Reflex Stimulation (BRS) External Power Supply 104 is a medical grade power supply that is used to supply 24-volt DC power to the BRS Module 108 (described hereinbelow).

(1-2) A probe 10x is used to administer and measure the genital stimulation in a manner as described in previous embodiments hereinabove. The tip 34x in the probe 10x may be replaceable and may contain an ID chip 112. The ID chip 112 is used to prevent its tip 34x from being used more than once (e.g., prevented from being used on more than one patient) as is described further hereinbelow. Thus, instead of the entire probe 10x being non-reusable on different patients, only the probe tip 34x is non-reusable. The probe 10x interfaces to the BRS Module 108 (which includes an amplifier/filter 36x having substantially identical function to the combination of the SEMG 35 and the amplifier 36 disclosed in FIG. 1 and described hereinabove). In particular, the amplifier/filter 36x includes a surface EMG amplifier/filter 116 for receiving signals from the electrodes 2, and a stim(ulus) probe amplifier 120 for receiving signals indicative of probe 10x activation (via cable 38x. Both amplifiers 116 and 120 are described hereinbelow.

(1-3) The ID chip 112 provided in the probe tip 34x can output data to the BRS module 108 for determining whether the probe tip has been previously used to contact a patient, and if so, the elapsed time since this first use. In one embodiment, such data includes a time and date that the probe 10x was first activated, or if not previously used such data may include a predetermined value such as zero. Thus, the ID chip 112 includes a non-volatile data storage for storing data indicative of the probe tip's activation history (which may be only the initial date and time of, if any, the probe tip's first activation). In one embodiment, such activation history may include the time and date of each activation, and/or the elapsed time of each activation. Note that the ID chip 112 may be activated each time the probe 10x is operably connected to the BRS module 108. In particular, data is communicated on the conductors 160a and 160b from the MCU 128 processor (described below) for activating the ID chip 112 so that it will respond to the MCU with an acknowledgement of whether the probe tip 34x can or cannot be used for a subsequent patient contact. Accordingly, an acknowledgement by the ID chip 112 that the probe tip 34x cannot be used will cause the MCU 128 to issue commands to at least prevent data collection from the probe 10x, and preferably provide an indication to the operator that the probe having this tip cannot be used for such data collection. There are various ways to provide such an indication of probe non-use, e.g., visual display on the BRS module 108 may be used such as a red LCD may light when the probe cannot be used, and a green LCK may light when the probe can be used. Alternative/additional visual and/or auditory presentations are also within the scope of the present disclosure. Accordingly, iconic and/or textual information can be visually presented to an operator for indicating whether the probe 34x (with its current probe tip 34x) can be operably used. Alternatively and optionally, synthetic speech or various sounds may be used for indicating whether the probe 34x (with its current probe tip 34x) can be operably employed.

(1-4) The BRS Module 108 is the interface unit between the BRS Computer 40x and both the patient applied probe 10x and EMG leads (collectively labeled as 46x in FIG. 6). Subsystems/components of the BRS Module are as follows:

(1-4.1) Micro Controller Unit (MCU) 128.

The MCU 128 is a microprocessor that controls and monitors data and communication in the BRS Module 108. The MCU 128 contains firmware for the following functions:

a. Connects and communicates with the BRS computer 40x via the USB interface 132.

b. Upon command the MCU 128, collects digital data from the surface EMG analog to digit converter 136 (which converts the amplified voltage differences from the electrodes 2 to digital data), and the Stim Probe analog to digital converter 140 (which converts the amplified probe activation signal to digital data). The MCU 128 then sends such digital data to the BRS computer 40x via the USB interface 132, c. Monitors the 24-volt power supply 104 and communicates the status of this power supply to the BRS computer 40x via the USB interface 132.

d. Reads and updates the IC chip 112 in the Stim Probe Tip 34x to ensure that the Probe Tip is not used for more than 30 minutes.

(1-4.2) Isolation DC/DC Converters 144.

The Isolation DC/DC converters 144 supply isolated −3.3 V, +3.3 V, and 5 V DC power to the patient connected components; in one embodiment, such converters may be: a Datel UWR-5/2000-D24E-C Murata NDTD0503C or similar components as one of ordinary skill in the will understand.

(1-4.3) Isolation Barrier 148.

The Isolation Barrier 148 provides the necessary creepage and clearance distances between the AC mains connected power and patient connected power.

(1-4.4) Power Detector 152.

The power detector 152 is used by the microprocessor MCU 128 to monitor the state of the 24 Volt Power supply from the power supply 104.

(1-4.5) Digital Optical Isolators 156.

The Digital Optical Isolators 156 are used to provide isolation between the patient connected electronics (i.e., the electrodes 2 and 4), and USB powered electronics (i.e., the computer 40x). The optical isolators 156 allow the MCU 128 to communicate with the analog to digital converters 136 and 140, and the chip 112 in the Stim Probe Tip 34x via a one wire interface provided by the conductors 160a and 160b.

(1-4.6) Stim Probe Amplifier/Filter 120.

The Stim Probe Amplifier/Filter 120 amplifies and filters the signal from the Stim Probe 10x to a level that can be read by the A/D converter 140. The MCU 128 controls the analog to digital conversion process of the A/D converter 140.

(1-4.7) Stim Probe A/D (Analog to Digital) Converter 140.

The A/D converter 140 is an analog to digital converter for changing the incoming amplified Stim Probe 10x signal into a digital value for the MCU 128. to read and then send to the computer 40x for analysis. The MCU 128 controls the A/D conversion process of the A/D converter 140.

(1-4.8) Surface EMG Amplifier/Filter 116.

The Surface EMG Amplifier/Filter 116 amplifies and filters the voltage signals from the electrodes 2 to a level that can be read by the A/D converter 136.

(1-4.9) Surface EMG A/D (Analog to Digital) Converter 136.

The converter 136 is an analog to digital converter for changing the incoming amplified Surface EMG signal into a digital value for the MCU 128 to read and send to the computer 40x for analysis.

(1-4.10) Signal Conditioner 164.

The signal conditioner 164 translates the two wire interface 160a from the MCU 128 to/from the 1 wire interface 160b which communicates with the ID chip 112.

(1-5) Computer 40x.

The computer 40x provides a user interface for displaying, e.g., displays such as shown in FIG. 5 described hereinabove. The computer 40x communicates with the BRS Module 108 through the USB interface 132. The computer 40x contains a custom application for at least the following functions:

a. Communicates and receives status information from the BRS Module 108 regarding power on (more generally activation status), information for obtaining probe tip ID chip 112 information (e.g., BCR time series values, ID chip status, etc.).

b. Sends commands to the BRS Module 108 to acquire data from the Stim probe 10x.

c. Graphs and/or analyses data from the Surface EMG data channel (which includes the components 116, 136, 156, and 128), and from the Stim Probe data channel (which includes the components 10x, 38x, 120, 140, 156, and 128) for presentation to an operator. The graphs and/or analysis performed may be as described hereinabove regarding the analysis process 60 (FIG. 1) and the user interface of FIG. 5.

d. Processes the Stim probe 10x signal to determine the time of commencement of patient stimulation.

e. Allows an operator to input patient and physician information.

f. Stores test case data for later review and analysis.

g. Prints reports is instructed by an operator.

(1-6) Printer 168.

The printer 168 is used by the Computer 40x to print reports on patient cases.

(2) High Level Processing of Data in the BRS Module 108.

For each of the EMG data channel (which includes the components 116, 136, 156, and 128), and the Stim Probe data channel (which includes the components 10x, 38x, 120, 140, 156, and 128) the high level algorithm used to process incoming analog data can be simplified down to:

(a) first inputting the analog data to an amplifier and a high pass filter (provided by the components 116 and 120), followed by a RMS detector process (provided by the A/D converters 136 and 140), and (b) providing the output from (a) immediately above to a process (provided by the computer 40x), wherein the data is decimated down from a 2 KHz sample rate to a 1 KHz sample rate by simply saving every other sample.

The signal provided by each of the above-identified channels passes through its own filter and RMS detector and decimator before being stored in the computer 40x (or a database operably connected thereto).

(2-1) Implementation.

Each high pass filter is implemented as a 4 pole Butterworth filter having a cutoff frequency of 10 Hz and a pass band ripple of 0%. Each RMS detector is implemented using the Root Mean Square algorithm for a finite number of sequential samples.

(3) Filter Algorithm

Each filter used in the amplifier/filter 36x may be a Chebyshev filter optimized for a pass band ripple of 0%, otherwise known as a Butterworth filter. Each of the filter is a form of recursive filter, which is also called an IIR (Infinite Impulse Response) filter. For a detailed description of recursive filters and the implementation see the Scientists and Engineers Guide to Digital Signal Processing chapters 19 and 20, by Steven W. Smith, published by California Technical Publishing.

(3-1) Implementation.

Each of the filters utilizes an embodiment of the following equation, as one of ordinary skill in the art will understand.

$$y[n]=a0x[n]+a1x[n-1]+a2x[n-2]+a3x[n-3]+ \ldots +anx[0]+b1x[n-1]+b2x[n-2]+b3x[n-3]+ \ldots +bnx[0],$$

wherein for $0<i<n$, ai is the recursion coefficient of the incoming signal, bi is the recursion coefficient of previous output signals, x[i] is the incoming signal, and y[i] is the output signal.

(4) RMS Algorithm

The RMS (Root Mean Square) is a measure of the magnitude of a varying quantity (e.g., a signal), which is calculated for a series of discrete values for a continuously varying function. The BRS software uses the RMS algorithm to transform the incoming signals into a magnitude (as opposed to a wave) so that the analysis by an operator easier. The period of the function is configurable by the operator. For a more detailed description of the RMS algorithm see http://en.wikipedia,org/wiki/Root_mean square.

(5) Stimulation Marker Detector Algorithm.

The Stimulation Marker Detector algorithm scans the stimulation probe time series (received via the cable 38x) looking for a change in signal amplitude of 1%±0.1% within a 50-millisecond window. If/when a change in amplitude at t+50 that exceeds this threshold is detected, a marker is placed in the data stream of the Stim Probe data channel, wherein the marker corresponds to time t. If a marker is detected, this algorithm is blacked out for a period of 1.5 seconds.

(5-1) Implementation

For each sample in the time-record (minus 50 mS) perform the following steps:

(5-1.1) Scan ahead of current position up to 50 mS;

(5-1.2) If the magnitude of the stimulus signal meets criteria, place a marker in the data stream of the Stim Probe data channel;

(5-1.3) Black out additional marker placement for 1.5 seconds

From the disclosure hereinabove, and the accompanying figures, it is believed that one of ordinary skill could manufacture the present screening system, and in particular, the probe (10 and/or 10a). More particularly, FIGS. 1 and 3 are believed to provide effective indications as to how the components of the embodiments of the probe would be assembled.

Figure 7:
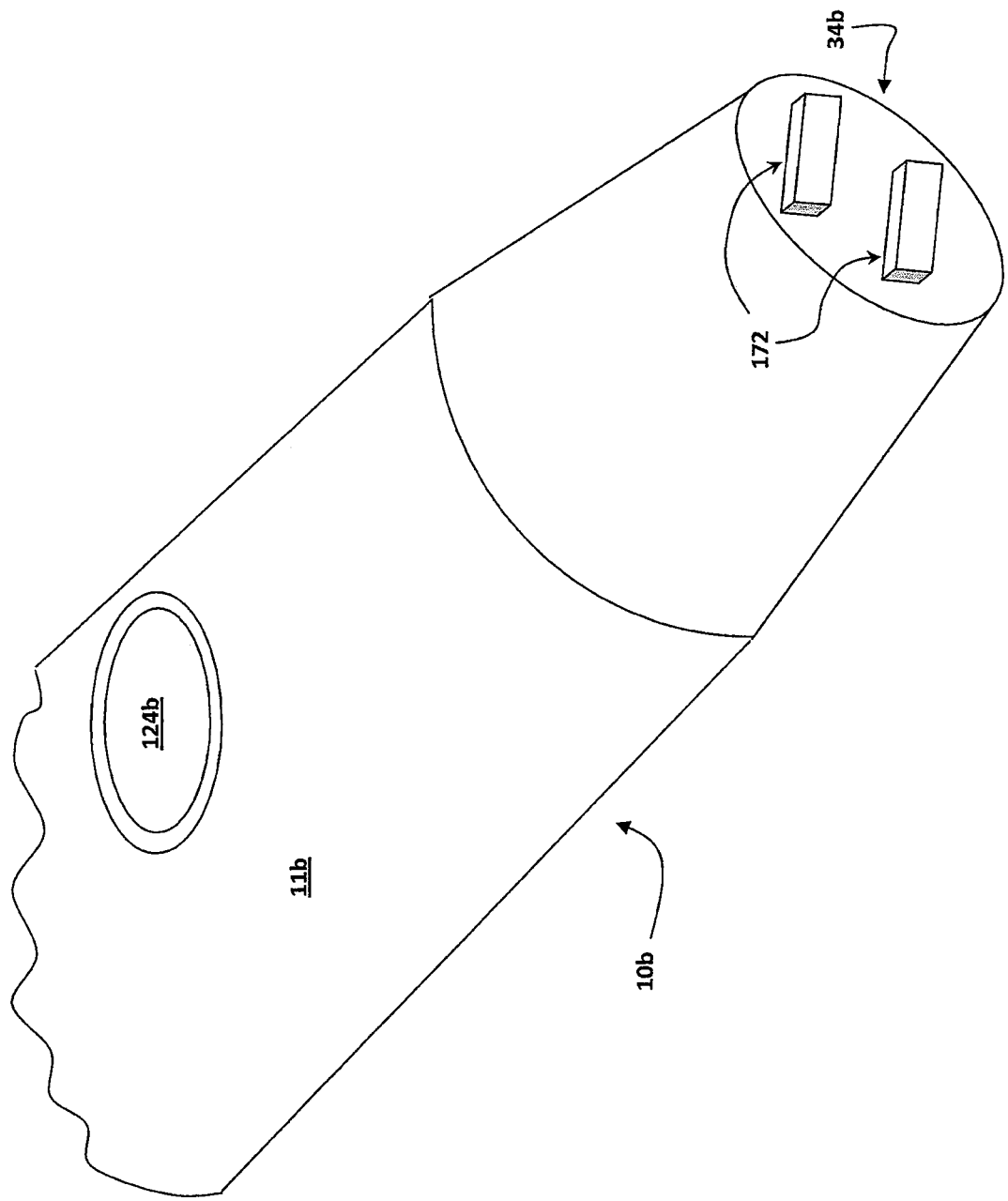
FIG. 7 shows another embodiment of the probe (10b) which may be used with a variation of the BRS module 108 shown in FIG. 6, wherein the identification chip 112 is not necessary to prohibit reuse of the probe with different patients.

Other embodiments of the probe are shown in FIGS. 7 and 8A and 8B, wherein components that functionally correspond to components of probe 10 and/or 10a described hereinabove are identified by the same numerical label except with an "b" following. Note that in each of the embodiments of FIGS. 7 and 8, a piezoelectric disk (12 or 12a) together with the pressure transferring components (e.g., the stimulus plunger (13 or 13a), the compression spring (15 or 15a), and the pressure transfer rod 78) of the probe embodiments 10 and 10a are not needed in the present embodiments of FIGS. 7 and 8A and 8B. Referring to the probe 10b of FIG. 7, the probe tip 34b includes two spaced apart electrodes 172 for conducting an electrical current therebetween during operation. In particular, when the button 124b is used to activate the probe 10b, a low difference in potential voltage is provided between the electrodes 172, and this difference is used to generate a small current between these electrodes when the probe tip 34b contacts the patient. In one embodiment, the operator of the probe 10b may provide an electrical conducting gel (not shown) on the patient's genital area where the probe tip 34b is to contact the patient. After application of the gel, the operator then contacts the genital area having the gel thereon for inducing a BCR response (the contact being, e.g., an abrupt, at least partially unanticipated genital contact of sufficient force to induce the BCR response). Accordingly, upon genital contact, a current between the electrodes 172 flows through the gel and can be used to capture data indicative of the time of contact at least as accurately as the embodiments of the probe 10 and 10a described hereinabove. It is believed that there are numerous examples of such gels that may be used during operation of the probe 10b, e.g., Electrode Jelly by Mavidon located at 1820 2nd Ave. No., Lake Worth, Fla. 3346, and/or Lectron II Conductive Gel.

Since the electrodes 172 may be fixedly attached to the tip 34b, and this tip fixedly attached to the probe handle 11b, the probe 10b of FIG. 7 may have no moving mechanical parts during operation. Moreover, the diaphragm (12 or 12a) of the previous embodiments as well as various shafts (e.g., 18 and 18a) and springs (e.g., 15, 15a, 118) are not needed in the probe 10b.

Embodiments of the probe 10b may be configured with various parameters. For example, the electrodes 172 may be spaced apart in a range of 1/16 of an inch to 7/16 of an inch. Additionally, the voltage difference between the electrodes 172 may be in the range of 0.25 Volts to 1.0 Volt, and more preferably from 0.3 Volts to 0.7 Volts. Note that any leakage of current from one of the electrodes 172 to the sensing electrodes 2 can be compensated for.

In the embodiment of FIGS. 8A and 8B, a deposable dielectric cap 176 can be provided over the tip 34b, wherein the cap has spaced apart electrically conductive leads 180 wherein each such lead contacts exactly one of the electrodes 172. Accordingly, since the leads 180 extend through the thickness of dielectric material of the cap 176, upon use of the probe 10b, the exterior conductive surfaces 184 of the leads will have the difference in voltage potential of the electrodes 172. Thus, when the surfaces 184 contact the conductive gel on the patient's skin, the current flowing (and/or the voltage difference drop) between the electrodes 172 can be detected in a similar manner as in the probe 10 and/or 10a embodiments above for thereby determining a delay in the resulting (if any) BCR.

Note that the cap 176 may be secured to the embodiment of the probe 10b (e.g., as shown in FIGS. 8A and 8B) by various techniques. In FIGS. 8A and 8B, the cap 176 has a circular ring 189 (having, e.g., a triangular cross section) projecting into the interior of the cap, wherein this ring snap fits into a corresponding circular detent 192 in the probe 10b. In other embodiments, ring 189 need not be continuous around the probe 10b, and may have a different cross section. Additionally or alternatively, alignment slots 192 may be provided in the probe 10b (alternatively, the cap) for mating with corresponding projections 195 from the cap 176 (alternatively, the probe).

In one embodiment of the cap 176, a cap stabilizer 198 may include an ID chip 112 as described hereinabove. In particular, the ID chip 112 can be in signal communication with an electrical fitting 199 for communicating with the BRS module 108 as described hereinabove.

FIGS. 9A and 9B show another embodiment of a cap (176c) together with another additional embodiment of the probe (10c), wherein components that functionally correspond to components of previous embodiments of the probe or the cap 176 described hereinabove are identified by the same numerical label except with a "c" following. FIG. 9 shows cap 176c for covering the probe tip 34c, wherein this cap has a shaft 188c which is slidable along axis 208c within a bore 192c through the cap 176c. Fixedly attached to the shaft 188c is an expanded portion 184c (which may be a disk or washer fixedly attached to the shaft), wherein the expanded portion is symmetric around the shaft 188c, and the axis 208c is the axis of the shaft 188c. A single electrical conductor 180c (which may be a circular ring attached to the expanded portion 184c, and concentric to the shaft 188c) is provided. An outer end of the shaft 188c is attached to a patient contact shield 196c for contacting a patient's genital area and thereby inducing a BCR; the shield covers the tip 34d, and according may be any of various shapes including hemispherical. An inner end of the shaft 188c has attached thereto an elastomeric component 200c such as a sponge-like material. The inner end of the shaft 188c and the elastomeric component 200c are received in a recess 204c within the probe 10c, wherein the shaft 188c is slidable along the axis 208c within the recess. Note that in the embodiment of FIGS. 9A and 9B, a piezoelectric disk (12 or 12a) together with the pressure transferring components (e.g., the stimulus plunger (13 or 13a), the compression spring (15 or 15a), and the pressure transfer rod 78) of the probe embodiments 10 and 10a are not needed in the present probe and cap combination. Moreover, as will be detailed more fully below, by taking of the advantages of one or more of the improvements shown in FIGS. 10-14, of an identification chip (112) may not be needed for limiting the reuse of the cap 176c.

During operation of the probe 10c with the cap 176c operably attached thereto as in FIGS. 9A and 9B, the elastomeric (or spring) component 200c fits within the closed end of the recess 204c and exerts a force effective for causing the expanded portion 184c to contact the interior of the cap 176c as shown in FIG. 9A, and accordingly provides space between the conductor 180c and at least one the electrodes 172c. When an operator activates the probe 10c (via, e.g., the button switch 124c), the space between the electrodes 172c and the conductor 180c is effective for preventing at least a predetermined detectable amount of a low voltage current (e.g., 0.25 Volts) from being communicated between the electrodes via the conductor. Subsequently, when the operator abruptly forces the contact shield 196c into contact with the patient's genital area, the shaft 188c slides along the axis 208c and thereby compresses the elastomeric component 200c by an amount effective for causing the conductor 180c to contact each of the spaced apart electrodes 176c. Accordingly, the current flow between (and/or voltage change at) the electrodes 176c can be detected for identifying a time indicative of the cap contacting the patient for inducing a BCR. Note that the cap 176c may be configured to substantially guarantee that the cap is only used once by providing mating slanted teeth 212c and 216c (FIG. 10), respectively, on the interior of the bore 192c and the shaft 188c so that the shaft slides easily within the bore for compressing the elastomeric component 200c, but does not (without substantial effort to the point of deforming the contact shield 196c) move in the opposite direction. Moreover, by providing such mating slanted teeth, the elastomeric component 200c may not be needed since these teeth alone may maintain the shaft and the conductor 180c in a spaced apart relationship to the electrodes 172c prior to use of the probe 10c and its cap 176c for inducing a BCR.

In another embodiment of the cap 176c may include a flat spring 220c provided along the shaft 188c as shown in FIGS. 11 through 13, wherein when the cap 176 has not been used to contact a patient (e.g., the shaft 188c is in its original position as in FIG. 9), the spring 220c is folded against the shaft as shown in FIG. 12. However, once the cap 176 has been used to contact a patient (and accordingly, the shaft 188c has been moved toward (or further into) the probe tip 34c (FIG. 9)), the free side 224c of the flat spring 220c is no longer confined to the bore 192c, and accordingly, expands away from the shaft 188c as shown in FIGS. 11 and 13. Thus, the expanded free side 224c of the spring 220c prevents the shaft 188c from being pulled back into its original position, and accordingly the cap 176 can be used only once. Note that one embodiment of the cap 176c the mating slanted teeth may be unnecessary when the free side of the flat spring 22c includes a bump 228c for mating with a detent, divot, slot, or other in detention 232c within the bore 192c as illustrated in FIG. 14.

Figure 15A:
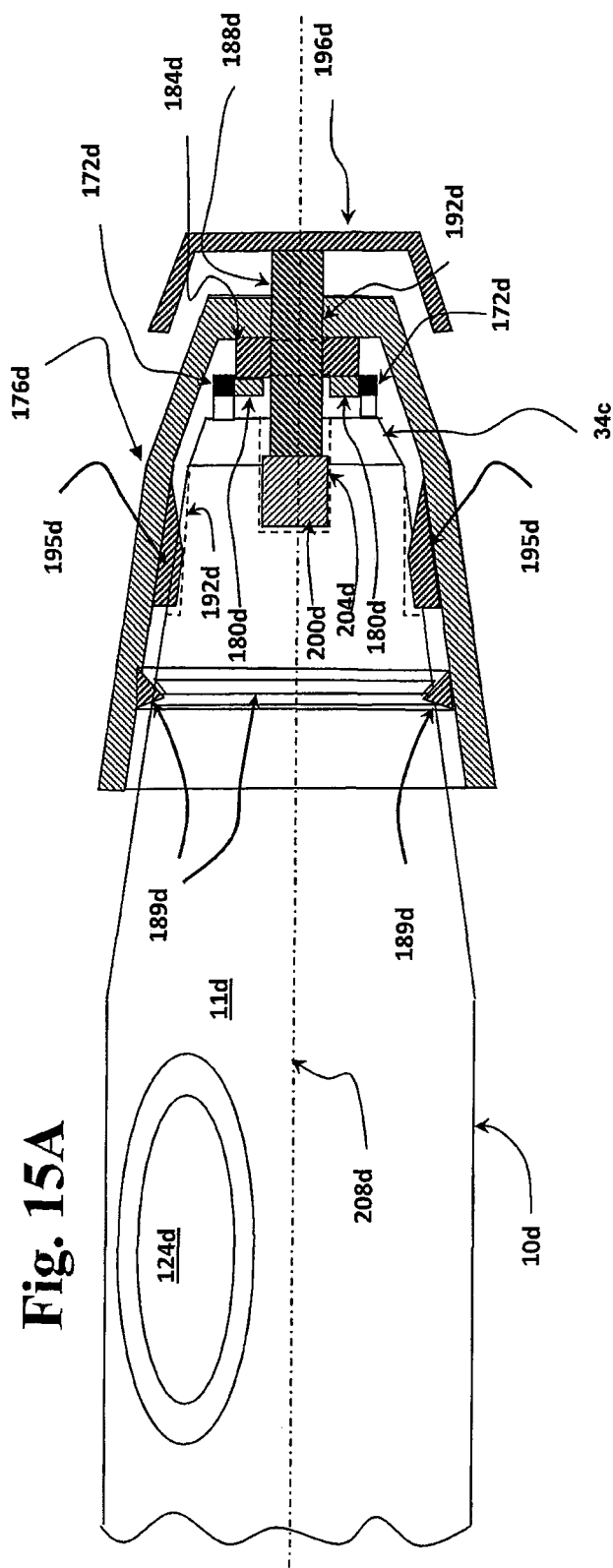
FIGS. 15A and 15B show another embodiment of a probe (10d) and a corresponding probe tip cap (176d) for supplying BCR characteristic signals to a variation of the BRS module 108 shown in FIG. 6. Note that FIG. 15A shows a cross section of the cap 176d.
Figure 15B:
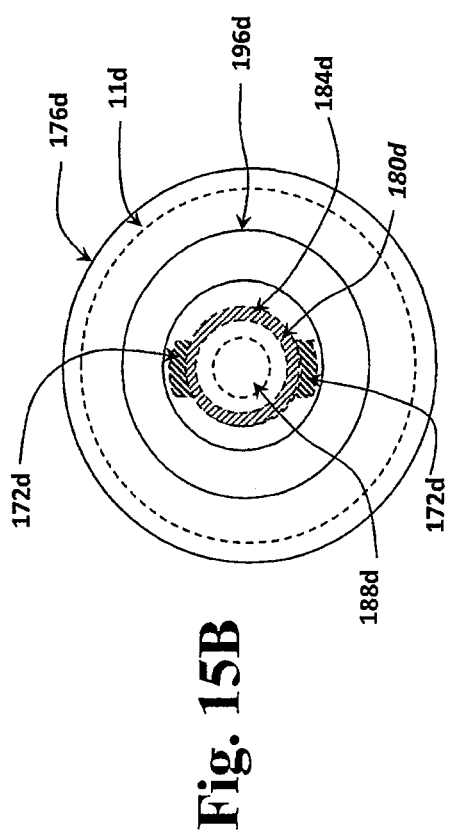
Figure 16:
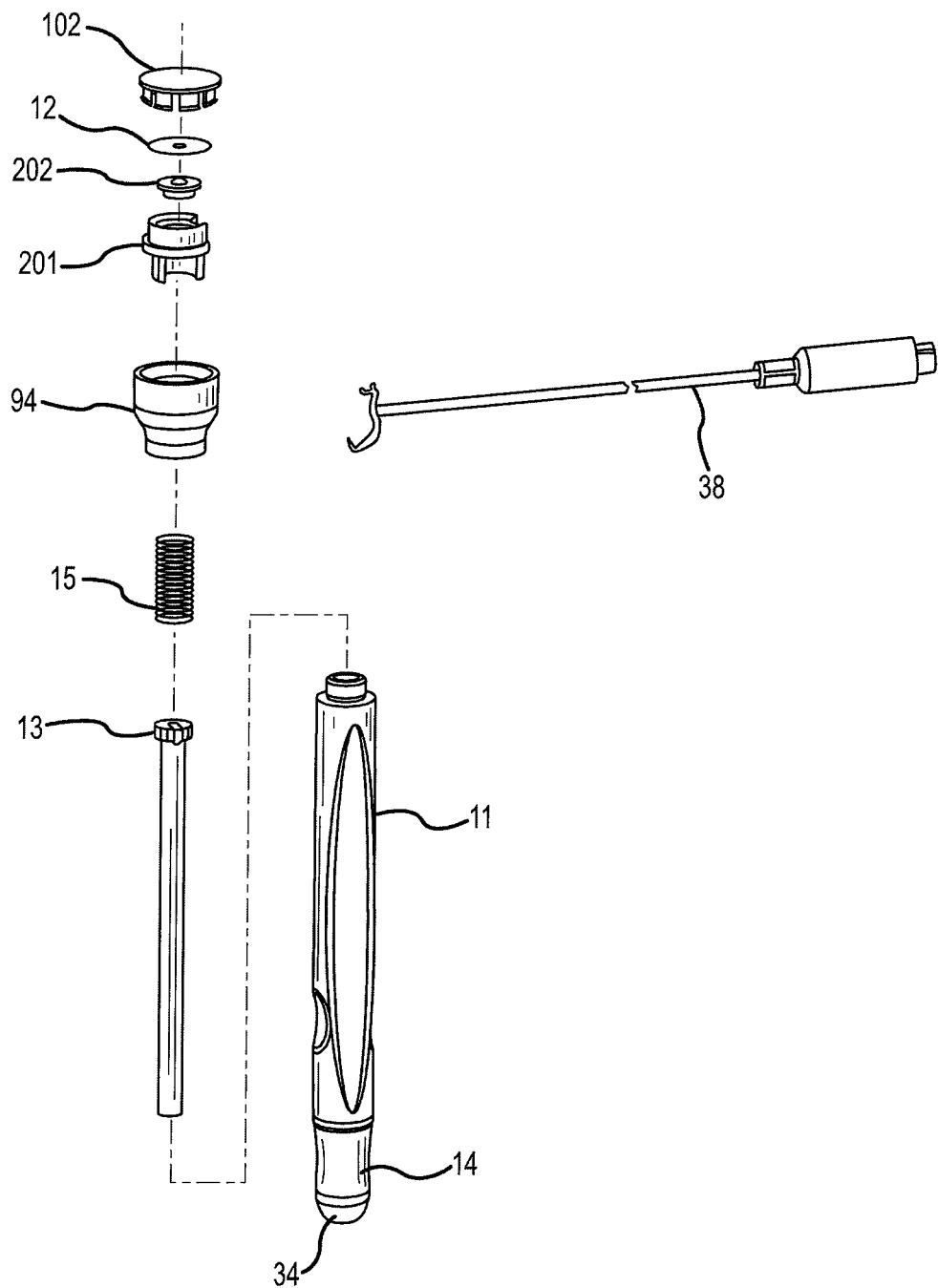
FIG. 16 is an exploded view of one embodiment of the present invention.
Figure 20:
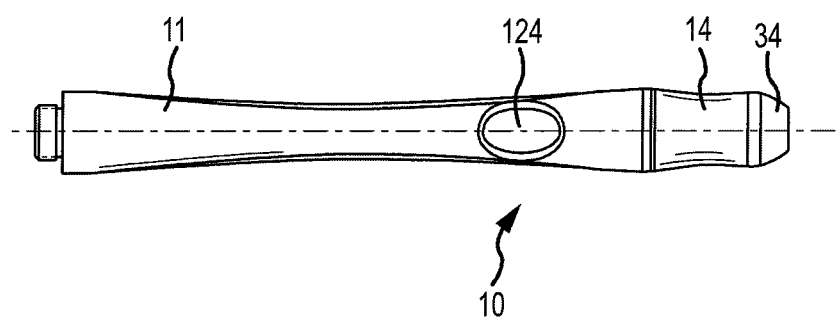
FIG. 20 is a perspective view of an embodiment showing a longitudinal axis.

Another embodiment of the probe (10d) and corresponding cap (176d) is shown in FIGS. 15A and 15B, wherein components that functionally correspond to components of previous embodiments of the probe (10, 10a, 10b, 10c) and the cap (176, 176c) described hereinabove are identified by the same numerical label except with a "d" following. FIGS. 15A and 15B show cap 176d for covering the probe tip 34d, wherein this cap has a shaft 188d which is slidable along axis 208d within a bore 192d through the cap 176c. Fixedly attached to the shaft 188d is an expanded portion 184d (which may be a disk or a washer fixedly attached to the shaft), wherein the expanded portion is symmetric around the shaft 188d, and the axis 208d is also the axis of the shaft 188d. A single electrical conductor 180d (which may be a circular ring attached to the expanded portion 184d, and concentric to the shaft 188d) is provided. An outer end of the shaft 188d is attached to a patient contact shield 196d for contacting a patient's genital area and thereby inducing a BCR; the shield covers the tip 34d, and according may be any of various shapes including hemispherical. An inner end of the shaft 188d has attached thereto an elastomeric component 200d such as a sponge-like material. The inner end of the shaft 188d and the elastomeric component 200d are received in a recess 204d within the probe 10d, wherein the shaft 188d is slidable along the axis 208c within the recess. Note that in the embodiment of FIGS. 15A and 15B, a piezoelectric disk (12 or 12a) together with the pressure transferring components (e.g., the stimulus plunger (13 or 13a), the compression spring (15 or 15a), and the pressure transfer rod 78) of the probe embodiments 10 and 10a are not needed in the present probe and cap combination. Moreover, by taking of the advantages of one or more of the improvements shown in FIGS. 10-14, of an identification chip (112) may not be needed for limiting the reuse of the cap 176d.

During operation of the probe 10d with the cap 176d operably attached thereto as in FIGS. 15A and 15B, the elastomeric (or spring) component 200d fits within the closed end of the recess 204d and exerts a force effective for causing the expanded portion 184d to contact the interior of the cap 176d as shown in FIG. 15A. When the expanded portion 184d contacts the interior of the cap 176d as shown, the electrical conductor 180d simultaneously contacts both the electrodes 172d (each being represented by solid black squares in FIG. 15A). When an operator activates the probe 10c (via, e.g., the button switch 124c), a low voltage current (e.g., 0.25 Volts) is able to flow between the electrodes 172d if the cap 176d is properly fitted to the probe 10d. Accordingly, an LED, or other light emitting device can provide the operator with positive feedback that the probe 10d and cap 176d are properly coupled for use. Upon forcefully and/or abruptly contacting a patient's genital area, the electrical conductor 180d moves toward the tip 34d, and accordingly slides past the electrodes 172d so that the flow of current between the electrodes ceases. The detection of the cessation/reduction of current flow and/or the increase in voltage at one or more of the electrodes 172d can provide a signal effective for commencing the timing of the delay in the (any) corresponding BCR. Note that, as with previous embodiments of the cap 176d, it may be configured to substantially guarantee that the cap is only used once. In particular, the various techniques described hereinabove (e.g., slanted teeth, flat spring, etc.) may be also incorporated into the cap 176d.

The invention illustratively disclosed herein suitably may be practiced in the absence of any element which is not specifically disclosed herein. It is apparent to those skilled in the art, however, that many changes, variations, modifications, other uses, and applications of the invention are possible, and also changes, variations, modifications, other uses, and applications which do not depart from the spirit and scope of the invention are deemed to be covered by the invention, which is limited only by the claims which follow.

The foregoing discussion of the invention has been presented for purposes of illustration and description. The foregoing is not intended to limit the invention to the form or forms disclosed herein. In the foregoing Detailed Description of Certain Embodiments of the Invention, for example, various features of the invention are grouped together in one or more embodiments for the purpose of streamlining the disclosure. The features of the embodiments of the invention may be combined in alternate embodiments other than those discussed above. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Detailed Description of Certain Embodiments of the Invention, with each claim standing on its own as a separate preferred embodiment of the invention.

Moreover, though the description of the invention has included description of one or more embodiments and certain variations and modifications, other variations, combinations, and modifications are within the scope of the invention, e.g. as may be within the skill and knowledge of those in the art, after understanding the present disclosure. It is intended to obtain rights which include alternative embodiments to the extent permitted, including alternate, interchangeable, and/or equivalent structures, functions, ranges, or steps to those claimed, whether or not such alternate, interchangeable, and/or equivalent structures, functions, ranges, or steps are disclosed herein, and without intending to publicly dedicate any patentable subject matter.

The invention claimed is:

1. A method for diagnosing at least one of a brain injury and a spinal cord injury, comprising:
   providing a probe comprising:
      a housing with a bore therethrough, the housing comprising a piezoelectric disk, the disk electrically connected to an amplifier and activated by a power source;
      a stimulus plunger having first and second ends and a shaft that extends through the bore, the shaft being movable along a longitudinal axis and having an expanded portion that prevents the stimulus plunger from sliding out of an opening in the housing; and
      a compression spring that biases the second end of the stimulus plunger away from contact with the piezoelectric disk,
      wherein, when the stimulus plunger makes non-invasive contact with a patient's genital area, pressure from the stimulus plunger is transmitted to the genital area to induce a bulbocavernosus reflex;
   placing the stimulus plunger in non-invasive contact with the patient's genital area;
   activating the piezoelectric disk to generate an electromagnetic response indicative of the non-invasive contact;
   using the electromagnetic response to identify at least one electrical response indicative of the bulbocavernosus reflex from a plurality of electrodes placed on the patient's skin adjacent to the genital area;
   determining at least one quantity selected from the group of a time delay between the electromagnetic response and the at least one electrical response, a time duration of the at least one electrical response, a value indicative of a magnitude of the at least one electrical response, and an attenuation in the at least one electrical response;
   comparing the quantity to a predetermined baseline;
   wherein the piezoelectric disk comprises an electrical switch; and
   wherein the electrodes are placed on opposite sides of the patient's rectum.

2. The method as set forth in claim 1, wherein the step of determining at least one quantity comprises a time delay between the electronic response and the at least one electrical response.

3. The method as set forth in claim 1, wherein the step of determining at least one quantity comprises a time duration of the at least one electrical response.

4. The method as set forth in claim 1, wherein the step of determining at least one quantity comprises a value indicative of a magnitude of the at least one electrical response.

5. The method as set forth in claim 1, wherein the step of determining at least one quantity comprises an attenuation in the at least one electrical response.

6. A method for diagnosing at least one of a brain injury and a spinal cord injury, comprising:
providing a probe comprising:
a housing with a bore therethrough, the housing comprising a piezoelectric disk, the disk electrically connected to an amplifier and activated by a power source;
a stimulus plunger having first and second ends and a shaft that extends through the bore, the shaft being movable along a longitudinal axis and having an expanded portion that prevents the stimulus plunger from sliding out of an opening in the housing; and
a compression spring that biases the second end of the stimulus plunger away from contact with the piezoelectric disk,
wherein, when the stimulus plunger makes non-invasive contact with a patient's genital area, pressure from the stimulus plunger is transmitted to the genital area to induce a bulbocavernosus reflex;
placing the stimulus plunger in non-invasive contact with the patient's genital area;
activating the piezoelectric disk to generate an electromagnetic response indicative of the non-invasive contact;
using the electromagnetic response to identify at least one electrical response indicative of the bulbocavernosus reflex from a plurality of electrodes placed on the patient's skin adjacent to the genital area;
determining at least one quantity selected from the group of a time delay between the electromagnetic response and the at least one electrical response, a time duration of the at least one electrical response, a value indicative of a magnitude of the at least one electrical response, and an attenuation in the at least one electrical response;
comparing the quantity to a predetermined baseline;
storing data indicative of a history of activation of the probe; and
determining a voltage difference between the plurality of electrodes.

7. The method as set forth in claim 6, wherein the step of determining at least one quantity comprises a time delay between the electronic response and the at least one electrical response.

8. The method as set forth in claim 6, wherein the step of determining at least one quantity comprises a time duration of the at least one electrical response.

9. The method as set forth in claim 6, wherein the step of determining at least one quantity comprises a value indicative of a magnitude of the at least one electrical response.

10. The method as set forth in claim 6, wherein the step of determining at least one quantity comprises an attenuation in the at least one electrical response.

11. A method for diagnosing at least one of a brain injury and a spinal cord injury, comprising:
providing a probe comprising:
a housing with a bore therethrough, the housing comprising a piezoelectric disk, the disk electrically connected to an amplifier and activated by a power source;
a stimulus plunger having first and second ends and a shaft that extends through the bore, the shaft being movable along a longitudinal axis and having an expanded portion that prevents the stimulus plunger from sliding out of an opening in the housing; and
a compression spring that biases the second end of the stimulus plunger away from contact with the piezoelectric disk,
wherein, when the stimulus plunger makes non-invasive contact with a patient's genital area, pressure from the stimulus plunger is transmitted to the genital area to induce a bulbocavernosus reflex;
placing the stimulus plunger in non-invasive contact with the patient's genital area;
activating the piezoelectric disk to generate an electromagnetic response indicative of the non-invasive contact;
using the electromagnetic response to identify at least one electrical response indicative of the bulbocavernosus reflex from a plurality of electrodes placed on the patient's skin adjacent to the genital area;
determining at least one quantity selected from the group of a time delay between the electromagnetic response and the at least one electrical response, a time duration of the at least one electrical response, a value indicative of a magnitude of the at least one electrical response, and an attenuation in the at least one electrical response;
comparing the quantity to a predetermined baseline; and
wherein the electrodes are placed on opposite sides of the patient's rectum.

12. The method as set forth in claim 11, wherein the step of determining at least one quantity comprises a time delay between the electronic response and the at least one electrical response.

13. The method as set forth in claim 11, wherein the step of determining at least one quantity comprises a time duration of the at least one electrical response.

14. The method as set forth in claim 11, wherein the step of determining at least one quantity comprises a value indicative of a magnitude of the at least one electrical response.

15. The method as set forth in claim 11, wherein the step of determining at least one quantity comprises an attenuation in the at least one electrical response.

* * * * *